United States Patent [19]
Salb

[11] Patent Number: 4,583,190
[45] Date of Patent: Apr. 15, 1986

[54] MICROCOMPUTER BASED SYSTEM FOR PERFORMING FAST FOURIER TRANSFORMS

[75] Inventor: Jesse Salb, New York, N.Y.

[73] Assignee: NeuroScience, Inc., Milpitas, Calif.

[21] Appl. No.: 370,484

[22] Filed: Apr. 21, 1982

[51] Int. Cl.$^4$ .......................... G06F 7/34; G06F 15/35
[52] U.S. Cl. ................................................... 364/726
[58] Field of Search ........ 364/726, 827, 200 MS File, 364/900 MS File; 343/5 FT

[56] References Cited

U.S. PATENT DOCUMENTS

| | | | |
|---|---|---|---|
| 3,731,284 | 5/1973 | Thies | 364/726 |
| 4,158,888 | 6/1979 | Shapiro et al. | 364/726 |
| 4,181,976 | 1/1980 | Collins et al. | 364/726 |
| 4,223,185 | 9/1980 | Picou | 364/726 |
| 4,266,279 | 5/1981 | Hines | 364/726 |
| 4,400,772 | 8/1983 | Broyles et al. | 364/200 |
| 4,438,488 | 3/1984 | Shibayama | 364/726 |
| 4,477,878 | 10/1984 | Cope | 364/726 |

OTHER PUBLICATIONS

Bhagat et al, "A High Performance Microprocessor-Based FFT Processor", IEEE Trans. on Ind. Electronics and Cntrl. Instrumentation, vol. IECI-25, #2, May '78, pp. 102-107.
Chwastyk, "A Fast Digital Spectral Analyzer", IEEE Trans on Instrumentation, vol. IM-20, #4, Nov. '71, pp. 198-201.
Intel, "MCS-48 TM Family of Single Chip Microcomputers User's Manual", Sep. '80, pp. 2-1-2-24.

*Primary Examiner*—James D. Thomas
*Assistant Examiner*—Dale M. Shaw
*Attorney, Agent, or Firm*—Kenyon & Kenyon

[57] ABSTRACT

A system for the on-line analysis and topographic display of human brain electrical activity which includes amplifying filtering and converter circuits for generating a plurality of signals, representing electrical activity at a plurality of predetermined data point locations on a patient's head in digital form, a first microprocessor and associated circuits to preprocess the digital signals into a predetermined format, and a second microprocessor and associated topographic map generator forming an image computation and display unit receiving the preprocessed digital signals as inputs from the image computation and display unit the topographic mag generator defining a map of a plan or elevation view of the brain containing a plurality of pixel points far in excess of the number of data points and interpolating the digital signals, so as to provide a value for each pixel on the map and providing the pixel information as outputs in synchronism with a horizontal and vertical scan, and a video monitor receiving the output of the image computation and display unit as an input.

8 Claims, 15 Drawing Figures

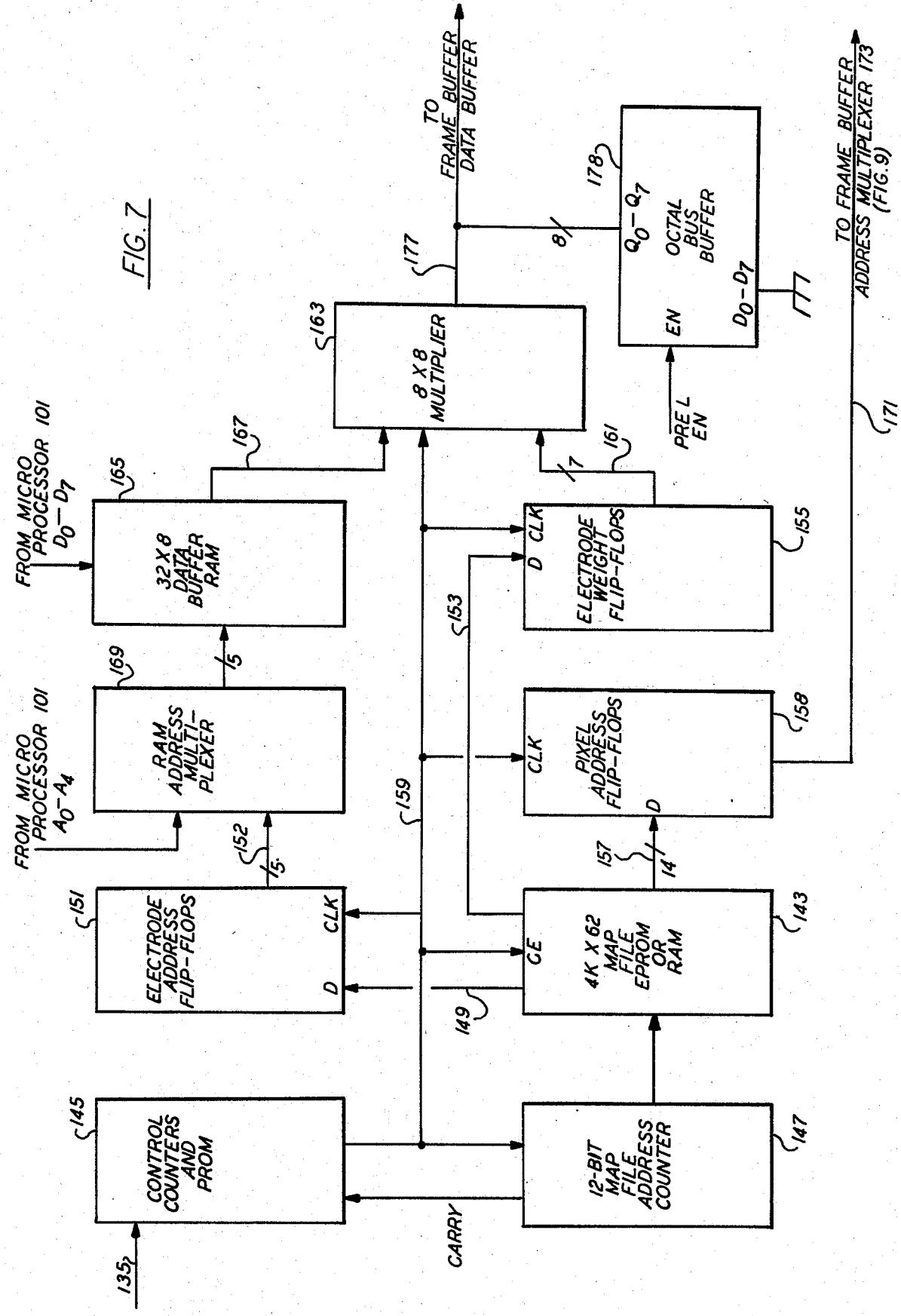

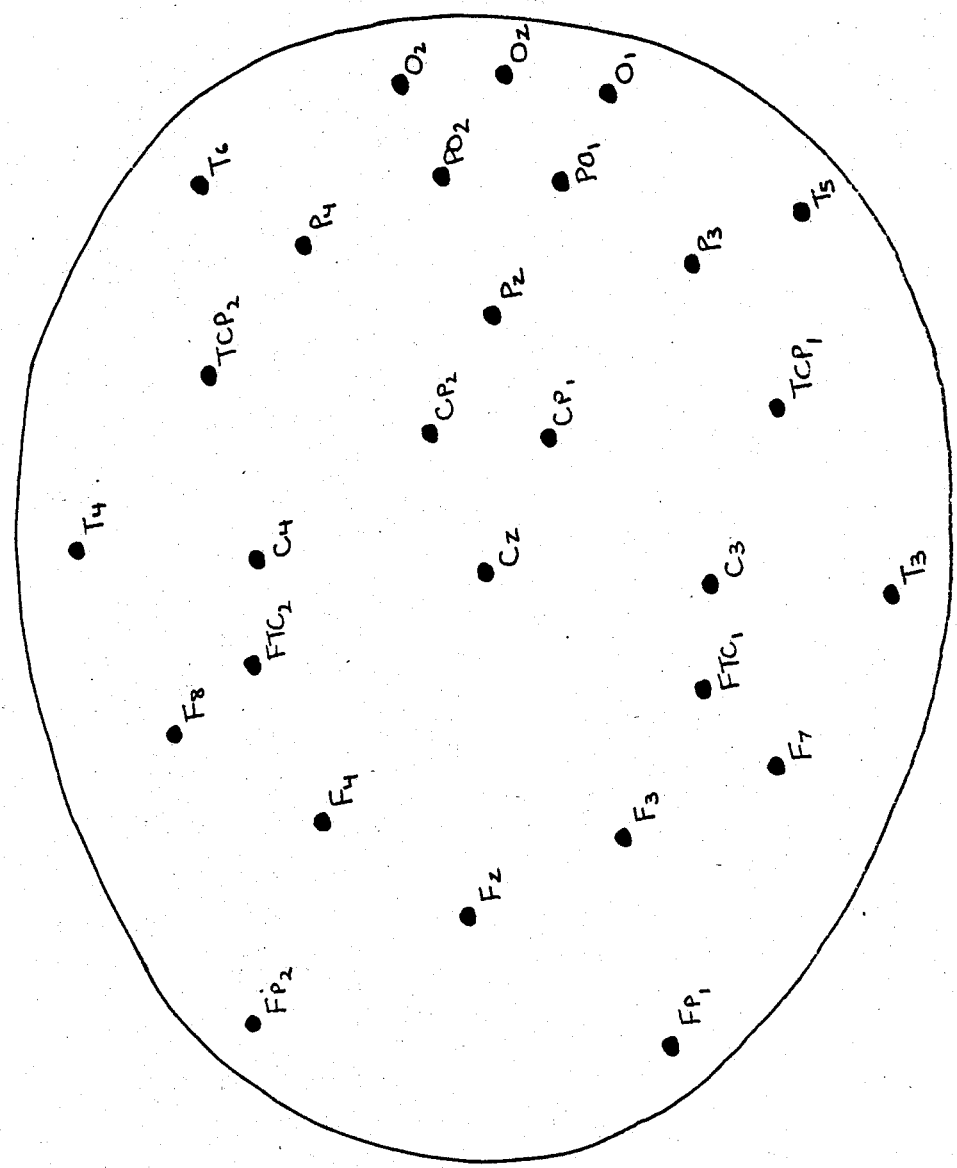

MICROCOMPUTER BASED SYSTEM FOR PERFORMING FAST FOURIER TRANSFORMS

BACKGROUND OF THE INVENTION

This invention relates to medical instrumentation in general and more particularly to an improved system for providing on-line acquisition, analysis and topographical display of the electrical activity generated by the human brain in real time.

The measurement of the electrical activity of the human brain and the preparation of an output representing this activity is known. A presentation, normally formed on a chart which has as one axis time and the other axis voltage, is known as an electroencephalogram (EEG). In order to develop an EEG one or more pairs of sensors are provided and attached to the subject's head. In a typical system, there can be a single reference electrode and as many as 16 other electrodes for each hemisphere of the brain. The result when recording data from these electrodes is a chart with up to 32 different traces which then must be analyzed by a neurologist, psychiatrist, etc. This, of course, is time consuming and in no case allows real time analysis.

Similarly, there have been attempts to provide a topographic display of brain activity. Such is carried out by obtaining data from electrodes and providing that data to a computer which then analyzes the data and provides output information for a topographic display. However, once again, a display of the brain activity which can be analyzed in real time is not possible. One can only look at the activity at predetermined points in time long after the brain activity has ceased.

The desirability and need for a device which will provide a topographical display in real time to neurologists, psychiatrists, etc. should be evident. With such a device, the physician can stimulate the patient and observe the reaction of the brain to various activities. Similarly, the condition of the brain in various states such as sleep, coma, etc. can be instantly observed by the physician. In addition, it is desirable that an instrument of this nature be capable of recognizing abnormal conditions and be able to store the display for reviewing after certain specified conditions take place.

Thus, it is the object of the present invention to provide a system which meets all these requirements.

SUMMARY OF THE PRESENT INVENTION

The present invention comprises a multiple microcomputer controlled system designed for the on-line acquisition, analysis, and topographic display of the electrical activity generated by the human brain known as the electroencephalogram (EEG). The system senses EEG signals through an array of disc electrodes temporarily affixed to multiple locations on the scalp, amplifies and filters the signals, and converts them to digital form. The digitized signals are analyzed in real time, using both software and special-purpose hardware, to extract features of neurological significance. The results of the real time analysis are transformed into a color-coded, anatomically accurate topographic map of brain activity by means of a special-purpose, high-speed hardware computation circuit. The topographic map is displayed dynamically (as a continously changing image), in real time, on a high resolution color video display monitor. The system is interactive, allowing the user to define the neurological features of interest to be detected and displayed, the display format, and other aspects of system operation. The rate at which the data is scanned and the moving image updated is under also under user control. Pattern recognition software allows the system to automatically detect and retain, for later examination, sequences of brain activity which have been predefined by the user to be unusual or abnormal.

The potential applications of this device are ubiquitous within the fields of neurology, neuropsychology, neurosurgery, anesthesiology, and psychiatry. The system, being microprocessor based, is compact and can easily be made portable. Its cost is relatively low, thus allowing widespread use in these areas.

BRIEF DESCRIPTION OF THE INVENTION

Figure 7A:
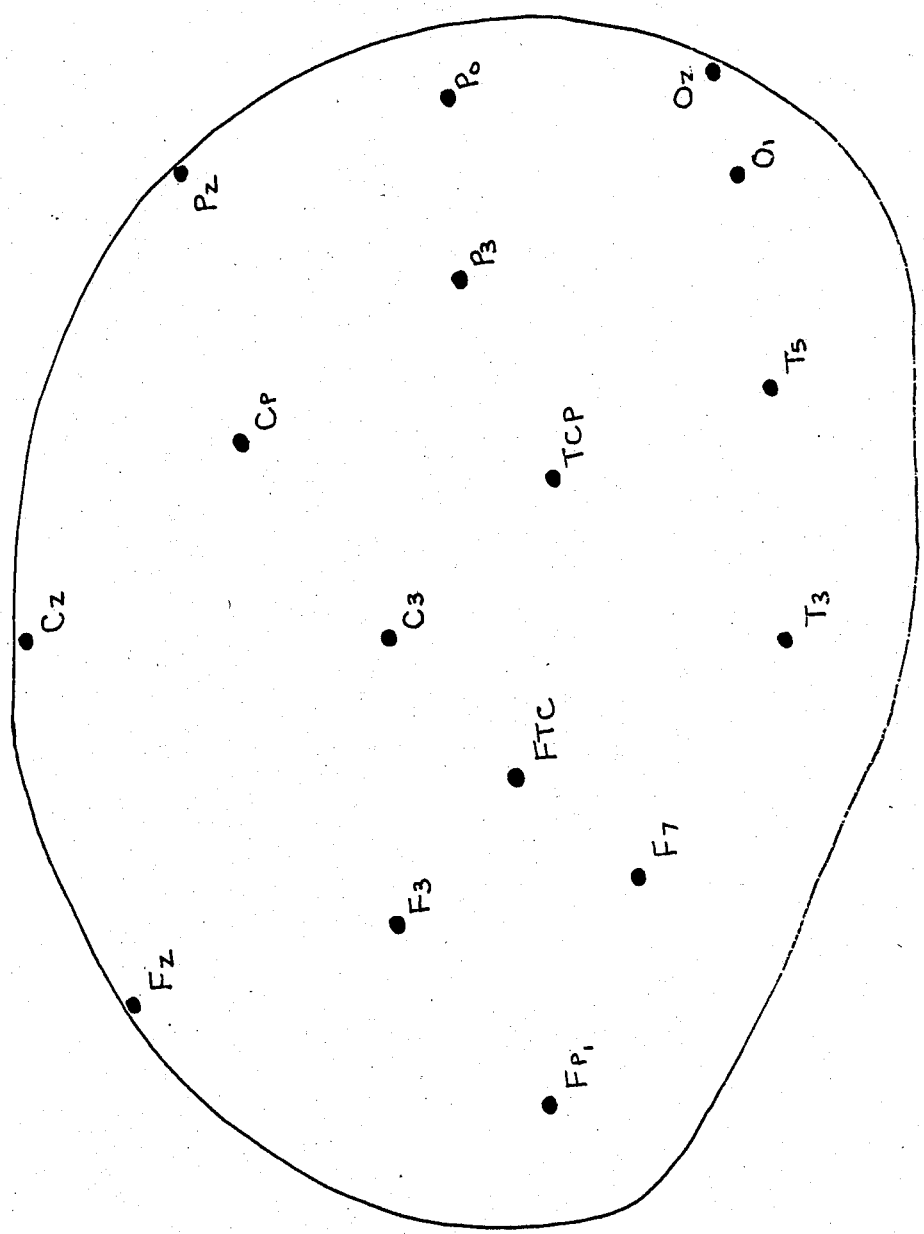

FIG. 7 is a block diagram of the topographic map generator. FIG. 7A is an elevation view of one hemisphere of the brain. FIG. 7B is a plan view of both hemispheres of the brain.

Figure 8:
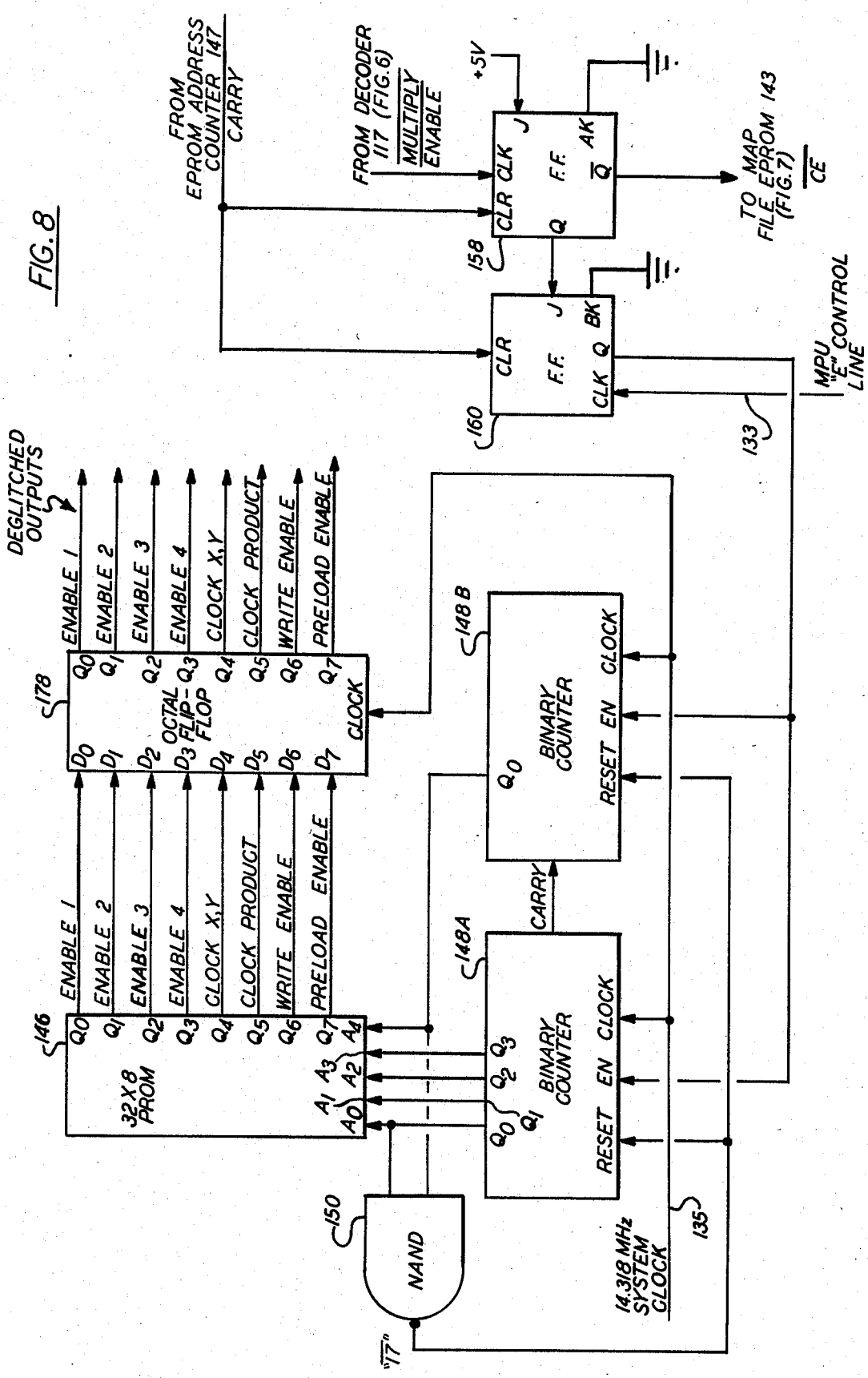

FIG. 8 is a detailed block diagram of the PROM of FIG. 7.

Figure 8A:
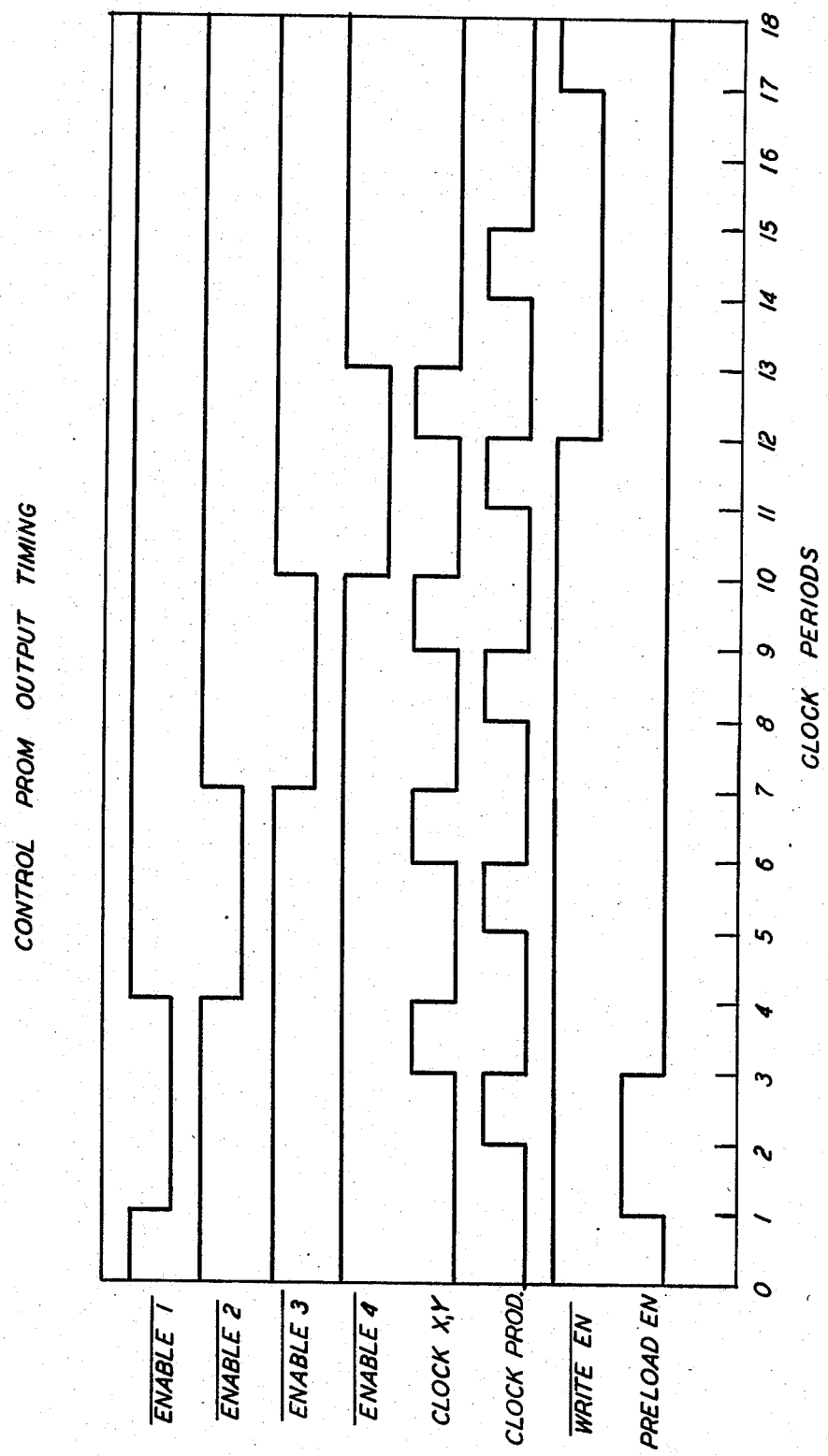

FIG. 8A is a timing diagram for FIG. 8.

Figure 9:
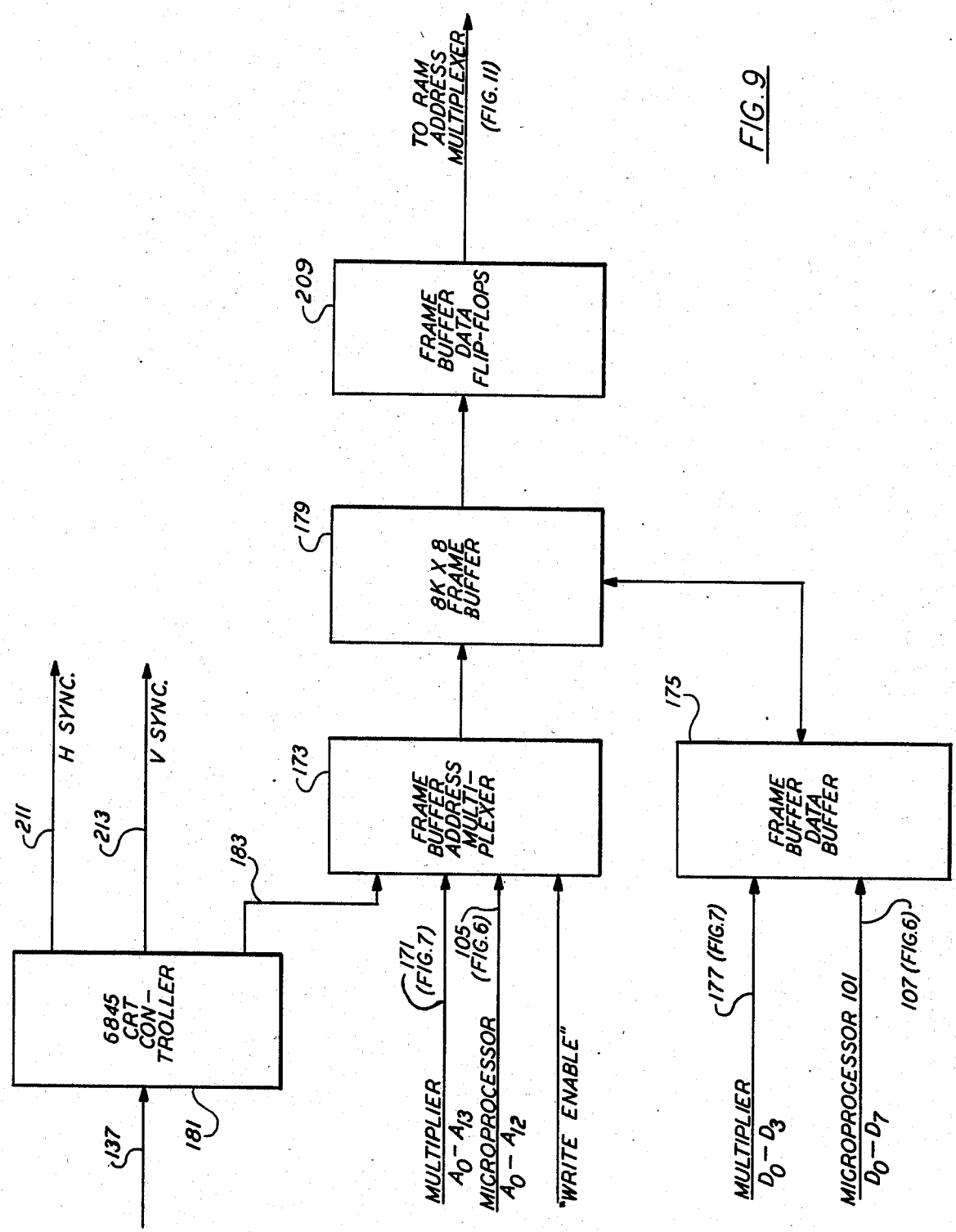

FIG. 9 is a block diagram of the video generator.

Figure 10:
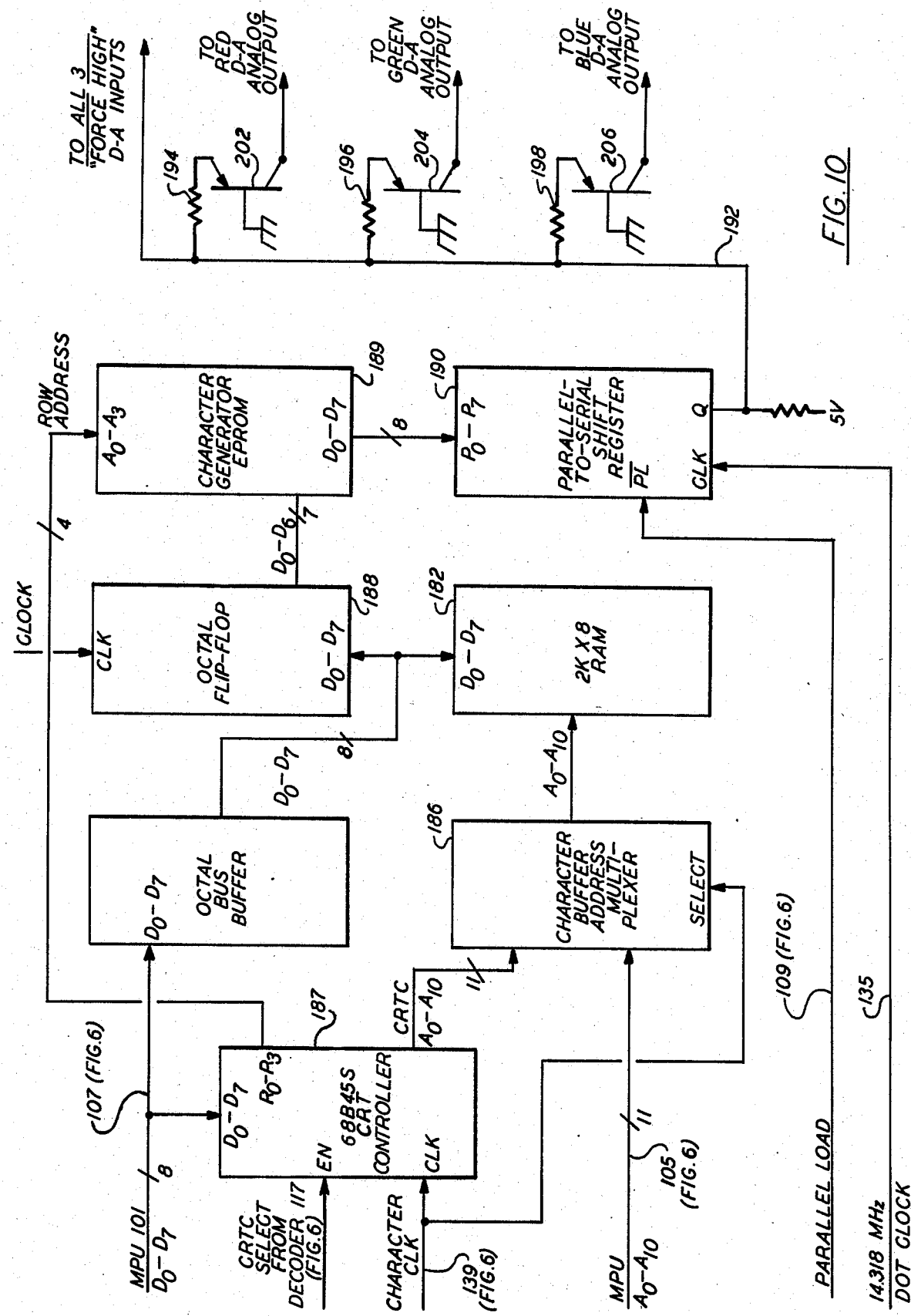

FIG. 10 is a block diagram of the character generator.

Figure 11:
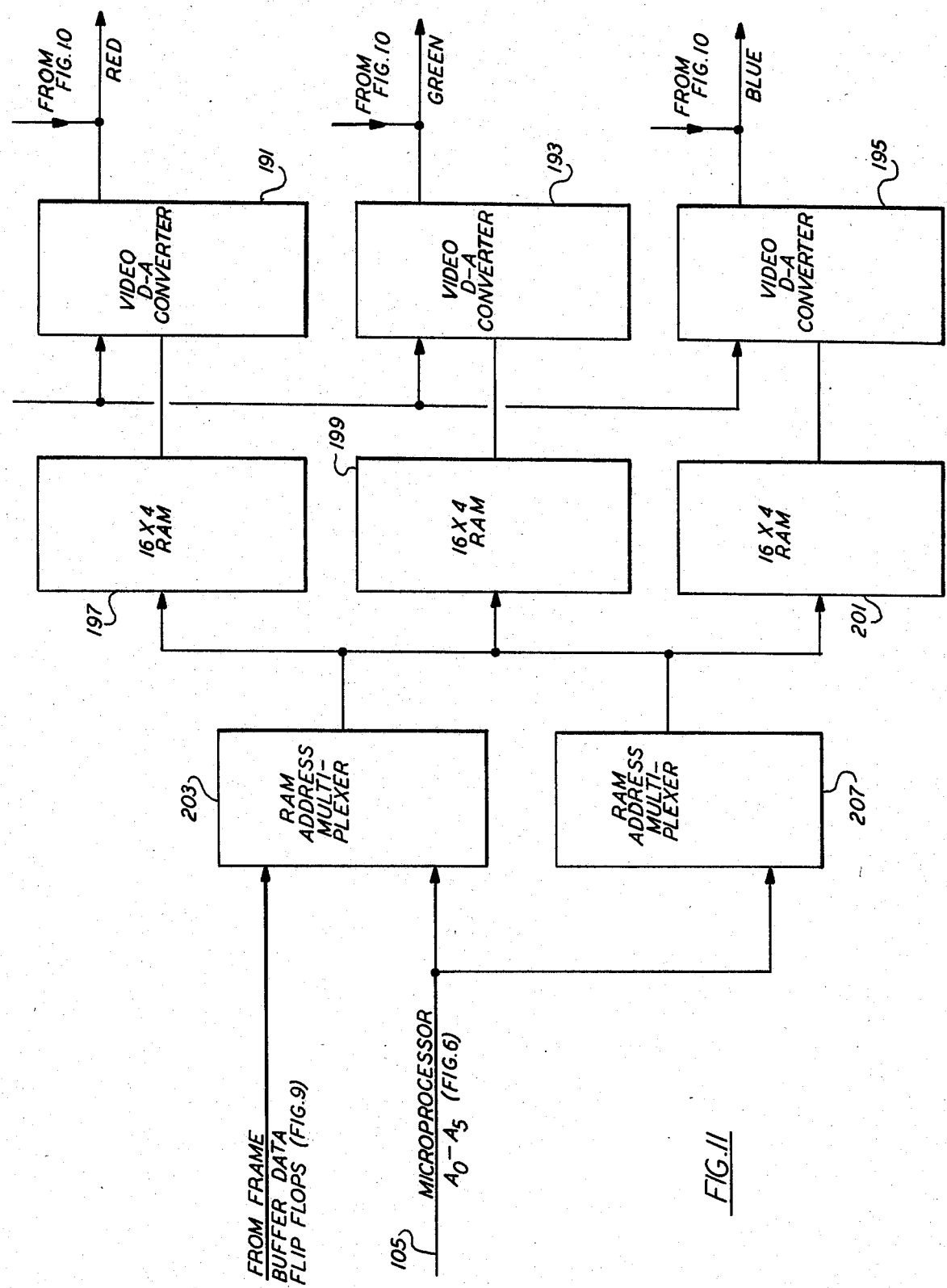

FIG. 11 is a block diagram of the video A/D converters.

Figure 12:
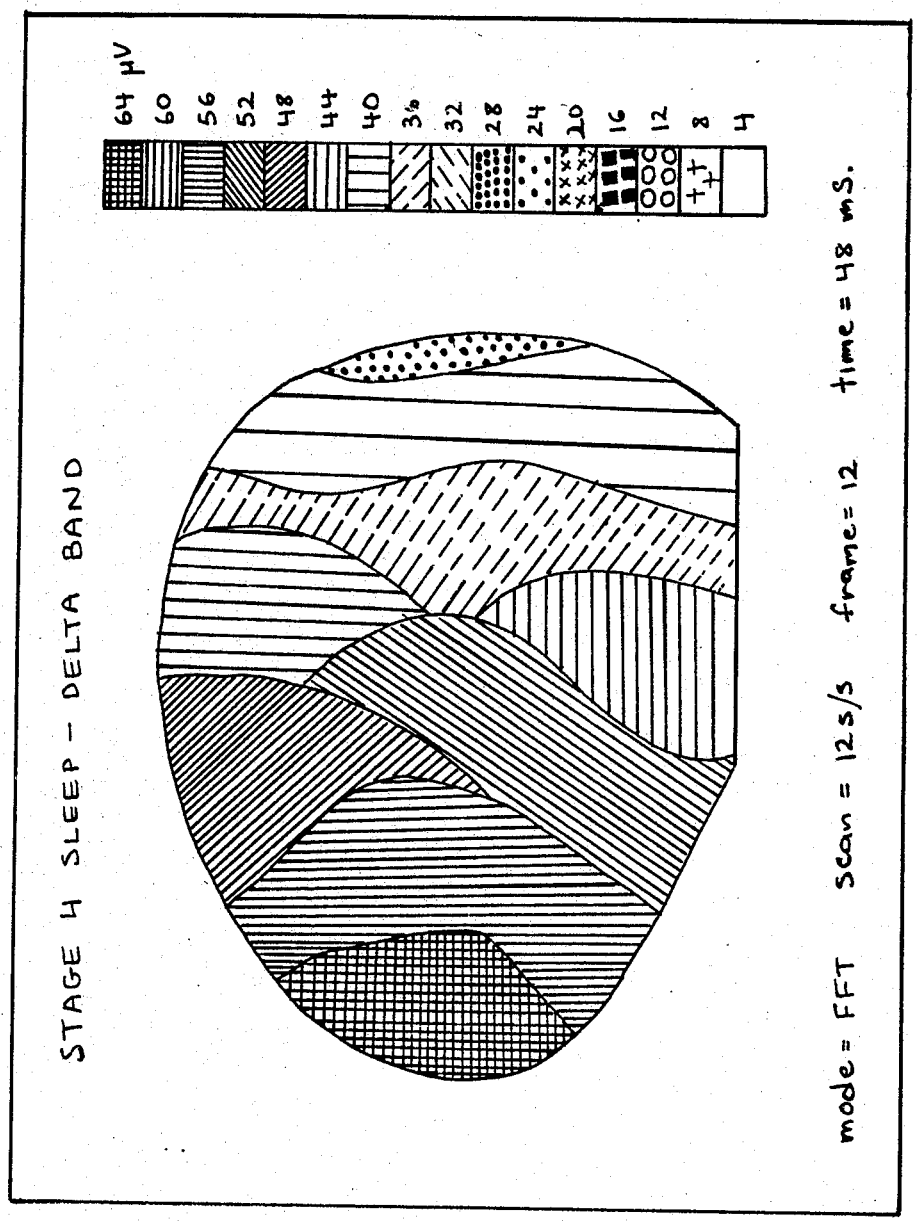

FIG. 12 illustrates a typical display.

DETAILED DESCRIPTION

Figures 1, 2:
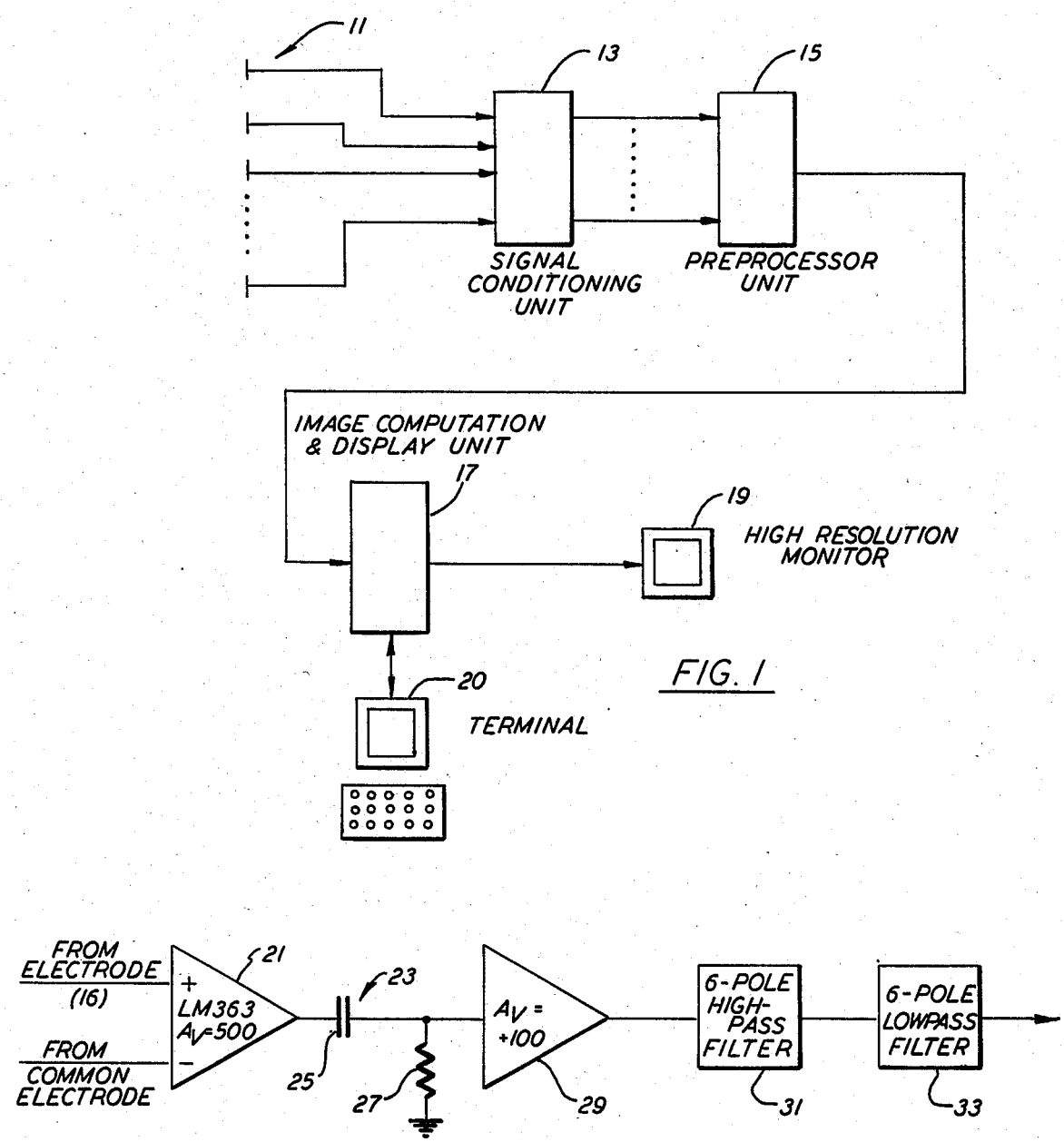
FIG. 1 is a block diagram of the system of the present invention.
FIG. 2 is a block diagram of one channel of signal conditioning.

FIG. 1 is an overall block diagram of the system of the present invention. Signals from electrodes 11, typically either 16 or 28 in number, are provided as inputs to an EEG signal conditioning unit 13. If only one hemisphere of the brain is being displayed there will be 16 inputs. If both hemispheres are to be displayed, two sets, or 28 inputs, will be provided, with 4 centerline electrodes common to both hemispheres. The signal conditioning unit contains either 16 or 28 channels, one for each input, in which signal preamplification and broad band filtering takes place. From this point on, the system will generally be explained in terms of 16 channels. However, it should be kept in mind that that number can be increased to present both hemispheres of the brain at the same time.

The outputs of the signal conditioning unit which will be 16 separate signals are provided to the EEG preprocessor unit 15. The preprocessor unit carries out the functions of signal multiplexing; analog to digital conversion; buffer storage of data; artifact detection; time domain analysis; frequency domain analysis; matched filter analysis; and evoked potential analysis. The resultant output, which will be analyzed data, is then fed to the image computation and display unit 17. Here the functions of topographic map generation; frame buffer storage; character generation, i.e., to display writing on the screen; color transformation; video digital-to-analog conversion; video sync generation and user interactive input/output are carried out. Further input to the image computation and display unit is over an RS 232 bus to a terminal 20 to permit the user to request various types of data and indicate when it is to be displayed. From the image and computation display unit 17, outputs of red, green and blue video along with a sync output are provided to a high resolution television monitor 19.

In general, incoming signals are preprocessed and multiplexed and converted into digital format. There is an artifact detection scheme in which particularly known interfering conditions are detected. Then, based on the operator's desire, analysis is done which can be either time domain analysis, frequency domain analysis, matched filter analysis, or evoked potential analysis. The result will be data corresponding to each of the 16 points, representing either time domain, frequency domain, matched filter or evoked potential activity. This information is, in the image computation display unit 17, put into a form which can be displayed on the high resolution display. In addition, terminal 20 is provided to permit control by the operator.

Various parts of the system will now be described in more detail.

SIGNAL CONDITIONING UNIT

As indicated previously, inputs to the signal conditioning unit are provided from electrodes 11. The electrodes, in conventional fashion, are affixed to the scalp of the subject using a temporary weak adhesive such as collodion. Alternatively, a commercially available cap with slots for the electrodes at the appropriate locations can be worn by the subject and the electrodes attached thereto. As indicated previously, for measurement of a single hemisphere 16 electrodes are required. The location of the electrodes is derived from the "10-20 system", an international standard of electrode placement universally accepted by neurologists and workers in allied fields. A number of additional electrodes are used on locations between the standard "10-20" electrodes to enhance spatial coverage of the scalp. The resistance of the scalp-electrode interface is diminished as much as possible by the application of a conductive electrode paste to the interface.

The electrodes are connected through shielded wires in a multi-pin connector to the amplifier channel. A separate amplifier channel is provided for each of the 16 electrodes. The first stage of amplification is an input amplifier 21 commonly known as an instrumentation amplifier and is required to amplify the extremely low-level signals in the presence of noise. An EEG is typically contaminated by 60 Hz interference which is capacitively coupled to the subject from surrounding AC wiring or other instruments, motors, etc. It is also contaminated by noise of biological origin such as muscle potentials from the subject's neck and face and DC offsets electrochemically generated at the electrode-skin interface. The instrumentation amplifier 21 has two ultra-high impedance inputs, a positive input and a negative input. The negative inputs to all 16 instrumentation amplifiers are connected to a single common electrode which is connected to the ear on the same side of the head as the 16 electrodes. This configuration is known as "common reference". The internal circuitry of the amplifier is particularly designed to give high common mode rejection so that signals appearing on both inputs will tend to be cancelled out within the amplifier. On the other hand, differential signals such as the EEG signal to be measured, present at the amplifier inputs, are amplified for example by 500 v/v resulting in a greatly enhanced signal to noise ratio. These amplifiers can be, for example, LM363 amplifiers made by the National Semiconductor Corp. or Analog Devices AD521 amplifiers.

The output of amplifier 21 is fed to a one pole filter 23 comprising a capacitor 25 and resistor 27. This filter has a minus 3 DB point of 0.03 Hz. Its purpose is to remove any DC offset generated at the electrode-scalp interface which has not been removed by amplifier 21. This filter output is coupled into a second amplifier 29 having a gain of approximately 100 v/v to result in a total amplification of the input signal of 50,000 v/v. This second amplifier may be a Precision Monolithic OP-15. The output of amplifier 29 is coupled first through a 6-pole high-pass filter 31 and then through a 6-pole low-pass filter 33. This provides a unity gain band pass filter passing the desired frequencies. The 6-pole high-pass filter 31 is a Sallen-Key filter with cut-off at 0.5 Hz. The 6-pole low-pass filter is a Sallen-Key filter with cutoff at 28 Hz. In conventional fashion, each filter section is constructed with 3 monolithic operational amplifier IC and discrete resistors and capacitors of 2% tolerance. Using this technique, an entire band pass filter is constructed with two National LM348 operational amplifier packages. Separate low-pass and high-pass filter sections are used in preference to a single-band pass filter in order to yield a flat pass band output and facilitate the separate tuning of the low-pass and high-pass cut-off points. As indicated previously, there will be 16 circuits of the type shown in FIG. 2. Thus, from the signal preamplification section there will be 16 outputs. These outputs are provided to the EEG preprocessor unit.

EEG PREPROCESSOR UNIT

Figure 3:
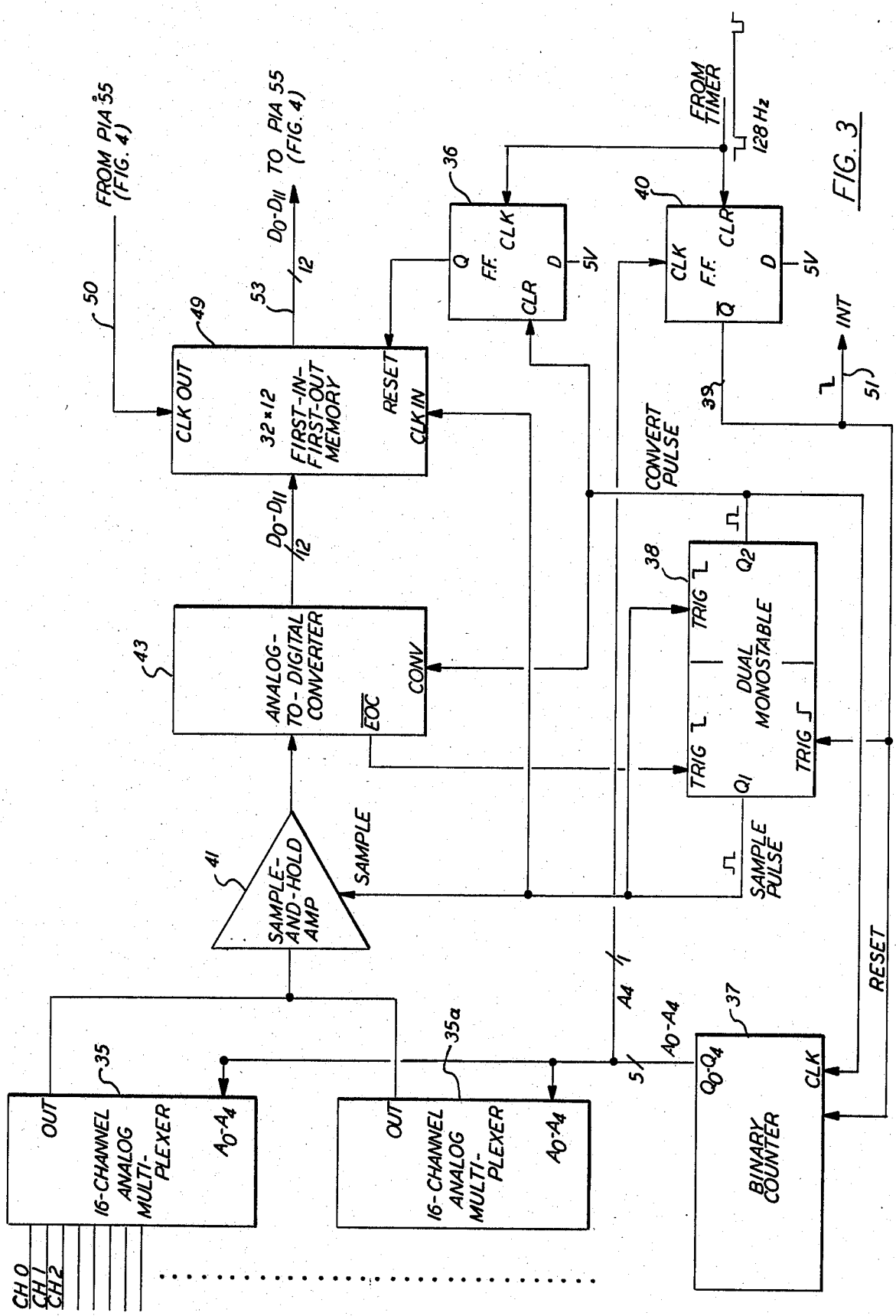
FIG. 3 is a block diagram of the preprocessor A/D conversion circuit.

As illustrated by FIG. 3, the 16 outputs from the signal processor are fed into a multiplexer. Shown is a multiplexer made up of two 16-channel sections 35 and 35a. These may be Precision Monolithics MUX-16 integrated circuits. The multiplexers sequentially connect each of the input signals to analog to digital conversion circuitry. The address or channel selection inputs of the multiplexers 35 and 35a are driven by a binary address counter 37 which may be an RCA CD4520. The counter is incremented at the end of each A to D conversion cycle. Using this circuitry, the first signal is connected to the A to D converter circuit, and a conversion is performed; the second signal is connected, a second conversion performed, and so on until all channels have been converted. A set of A to D conversions of all input channels is initiated by a signal generated by a timer within the preprocessor microprocessor microcomputer circuitry to be described below At the end of each complete conversion cycle, the multiplexer address counter 37 is reset to 0 by a signal on line 39 from the conversion flip-flop 40.

Analog to digital conversion is carried out utilizing a sample and hold circuit 41 and analog to digital converter chip 43. The sample and hold circuit may be a Burr-Brown SHC-80 sample and hold circuit and the converter itself a Burr-Brown ADC-80 12-bit A to D converter. Although 12-bit precision is not required for EEG signal analysis, the use of a 12-bit converter yields the dynamic range necessary for the widely varying amplitudes of typical EEG signals. Thus, both the signal of 5 microvolts peak and one of 200 microvolts peak can be measured with a resolution of one part in 4096, or well under 0.1 microvolts.

A typical conversion cycle is performed as follows. In the timer, a set of 2 CD40103 counters (not shown) divides down the 2 MHz microprocessor clock to 128 Hz, the sampling frequency. A negative pulse from the timer clears the conversion flip-flop 40 which, in turn, enables the multiplexer address counter 37 by removing the reset signal on line 39 and triggers a dual monostable multivibrator 38. The first section of monostable 38 fires, and sets the sample-and-hold 41 to the sample mode. The falling edge of the same pulse triggers the second side to initiate the A-D conversion cycle and sets the sample-and hold 41 to "sample". At the same time, it clocks into memory 49 the data at the output of converter 43. This is not good data the first time. To prevent this data from being stored, the "Reset" input to memory 49 is held high (the reset condition) by an output from flip-flop 36 which was set by the 128 Hz input pulse. The output pulse from the second side increments the multiplexer address counter 37 to the next channel address and initiates a conversion. This pulse from the second side also clears a flip-flop 36 to remove the "reset" input to memory 49. At the end of the conversion, the "end of conversion" (EOC) line of the A-D converter goes low, triggering monostable again 38 and repeating the whole conversion sequence. Since memory 49 is no longer in the "Reset" mode, the signal from the first half of the dual monostable, clocks the digitized A-D value into the 32×12 first-in first-out memory 49. On the first conversion, as noted above, this signal also clears flip-flop 36 which was set by the 128 Hz Clock to reset memory 49. When the multiplexer address counter has been incremented to its terminal count after 16 (28) conversions, it resets (clocks) the conversion flip-flop 40, disabling the conversion circuit until the next timer pulse 1/128 second later.

When all 16 signals have been converted, and the digital data entered into the first-in first-out buffer memory, a non-maskable interrupt signal (NMI) is sent to the microcomputer from the conversion flip-flop on line 51 notifying it that a complete set of data points is available for input. By operating in this manner, the micro-computer does not have to occupy itself with any aspect of the A to D conversion sequence once started, leaving it free to perform other tasks during this period. The program for the microcomputer is attached.

Although we have described the EEG preprocessor as deriving the data to be analyzed from electrode inputs, the preprocessor can also analyze data which has previously been converted from analog to digital form by external devices. In this case, the data would be input to the preprocessor through a 68B21 PIA in parallel digital format.

Figure 4:
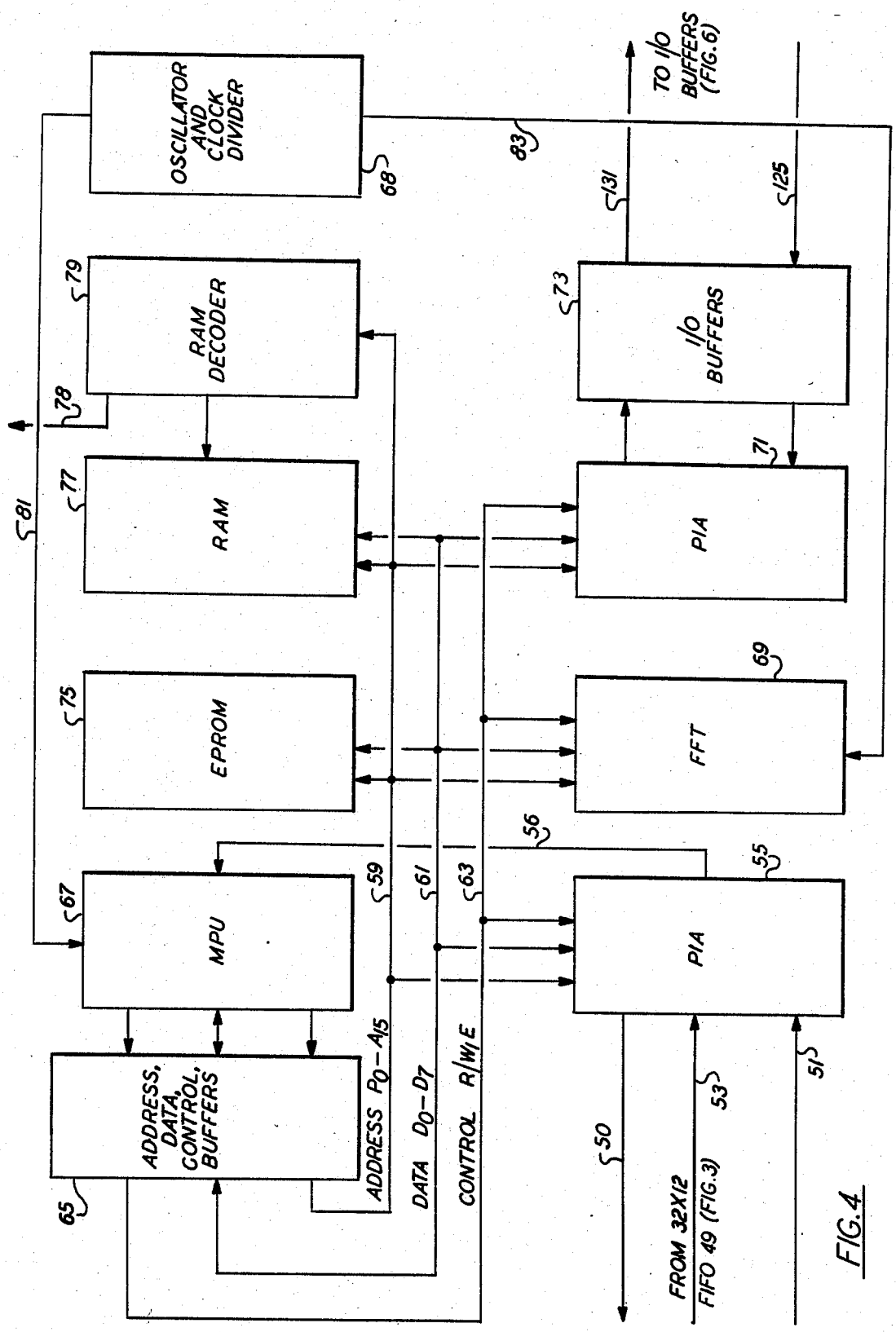
FIG. 4 is a block diagram of the EEG preprocessor micro-computer.

Referring now to FIG. 4, it can be seen that the 16 [or 28] digital outputs of the memory 49 are fed over line 53 to a peripheral interface adapter (PIA) 55 which may be a Motorola 68B21. Output takes place in response to a signal on line 50 of FIG. 3 from microprocessor 67 through PIA 55. In conventional fashion, three buses are provided for the microcomputer an address bus 59, a data bus 61 and a control bus 63. These three buses are coupled through address data and control buffers, indicated by block 65, to the microprocessor 67. Microprocessor 67 also receives an input from a clock 68 which generates the necessary timing. In addition, coupled to the three buses is a fast Fourier transform (FFT) module 69, a second peripheral interface adapter (PIA) 71, the output of which is coupled to buffers 73, an erasible PROM memory 75 and a random access memory (RAM) 77 and RAM decoder 79, the last being coupled only to the address bus. The erasible PROM memory 75, which may be an Intel 2732A 4K by 8 bit memory, is used to store the program. The random access memory which is a 20K memory can be made up of 2K by 8 bit CMOS Hitachi HM6116 RAMS. The oscillator and clock divider 68 can comprise a crystal oscillator and binary counter. The FFT circuit used in the present invention is a special circuit made by American Microsystems, Circuit No. S2814A.

The clock frequency for the micro-processor 67 which is fed over line 81 is 8 MHZ. The FFT processor is operated at 16 MHZ by a signal on line 83 from clock 68. The 8 MHZ clock frequency is obtained by dividing down the 16 MHZ signal fed to the FFT circuit 69. All microprocessor address and control lines are buffered by octal bus buffers, typically 74LS244, and data lines buffered by bi-directional octal bus transceivers, typically 74LS245, shown as block 65. The RAM address decoding is performed by two 3 to 8 decoders, typically 74LS138, in block 79.

The microprocessor 67 upon receipt of an interrupt signal on line 51 coupled through PIA 55 to line 56, begins inputting the 16 words from line 53 through the peripheral interface adapter 55. For most experimental situations, the sixteen data words are added and their average found. This average is subtracted from each data word. This computation converts the "common reference" configuration to an "average reference" configuration, which is generally considered superior for spatial analysis of EEGs. This information is stored in 16 separate data buffers in RAM 77 with each digital word occupying two bytes. The data buffers are arranged so they always contain the latest 512 digital conversions for each channel with the oldest samples continuously being discarded.

In carrying out time and frequency domain analysis, a 128 Hz conversion rate is used. Thus, 512 conversions at this frequency represent the last 4 seconds of activity in each channel. For the 256 Hz conversion rate used in the evoked potential analysis, 204 samples are input during each trial, so the data buffers contain the 0.80 second of activity following the stimulus. Once the data is stored, the program first carries out a step of artifact detection. This is a process for detecting noise and subject movement artifacts. Such artifacts can seriously contaminate the EEG data and lead to grossly erroneous measurements and results. First, the data in the data buffers is examined for evidence of these types of artifacts. In examining the magnitude of each of the data points, if saturation of a string of consecutive samples is found, i.e., excessive signal amplitude, this is an indication of subject motion, and an indication is given to the operator. Similarly, if a series of sequential data points having a changing slope at a very high frequency is detected this is indicative of high-frequency noise as are signals whose polarities change at a rate of above 40 Hz. The combination of tests for these conditions is sufficient to detect contamination of the signal by artifact in a great majority of cases.

As indicated previously, through the keyboard of Terminal 20—FIG. 1, the operator can select time domain anaylsis, frequency domain analysis, matched filter analysis, or evoked potential analysis. Time domain analysis is particularly useful in that it is similar to the process of visual analysis performed on a signal trace or plurality of signal traces by a trained neurologist or electroencephalographer. Time domain analytic techniques are concerned with the period, or duration, of the EEG waves, a wave being defined as the interval between successive negative to positive crossings of the iso-electric zero volts point by the signal. The peak-to-peak voltages of the waves, is defined as the voltage difference between positive maximum voltage and negative maximum voltage occurring during a single wave.

TIME DOMAIN ANALYSIS

In carrying out time domain analysis, the preprocessor micro-computer is programmed to search through each data buffer and identify successive waves. The waves are categorized by period and amplitude and a running total of total duration and total peak voltages is kept for four period categories. The standard categories are delta [330-1,000 ms], theta [125-330 ms], alpha [83-125 ms], and beta [50-83 ms]. Non-standard categories, or categories defined by a combination of period and amplitude are easily specified by the user from the keyboard. The program poses questions to the operator and other data than the topographic display is supplied to him on the display of terminal 20.

FREQUENCY DOMAIN ANALYSIS (FFT)

The operator can also select frequency domain analysis. Frequency domain analysis is a technique for measuring the electrical power present in the EEG over a spectrum of frequencies. The advantage of frequency domain analysis as compared to time domain analysis include the fact that it is better defined in classical mathematical signal processing terms. The disadvantage is the much more intensive computation necessary as compared to time domain techniques. The present invention accomplishes this intensive computation utilizing the FFT integrated circuit 69. Through the use of a separate hardware circuit to do this as opposed to a software solution, the computation can be carried out in real time. The microprocessor 67 transfers the data to the FFT block 69 and also specifies the sequence of computations that block 69 performs. This permits the preprocessor to perform other tasks while the block 69 is engaged in the FFT computation.

As in the case of time domain analysis, FFT analysis may be performed on either fixed adjacent sequences of digitized data or on a moving window of the data. Microprocessor 67 specifies the sequence of subroutines performed on this data by the FFT circuit 69. This arrangement permits the computation of the FFT in a far shorter time period than if the computation were performed by microprocessor 67 entirely in software. Using the arrangement described above, it requires approximately 1.0 second to perform the FFT computation on 16 channels of data, each consisting of 256 data points. If the computation were performed entirely in software by microprocessor 67, it would require many minutes of computation time, which would completely preclude real-time analysis.

Figure 5:
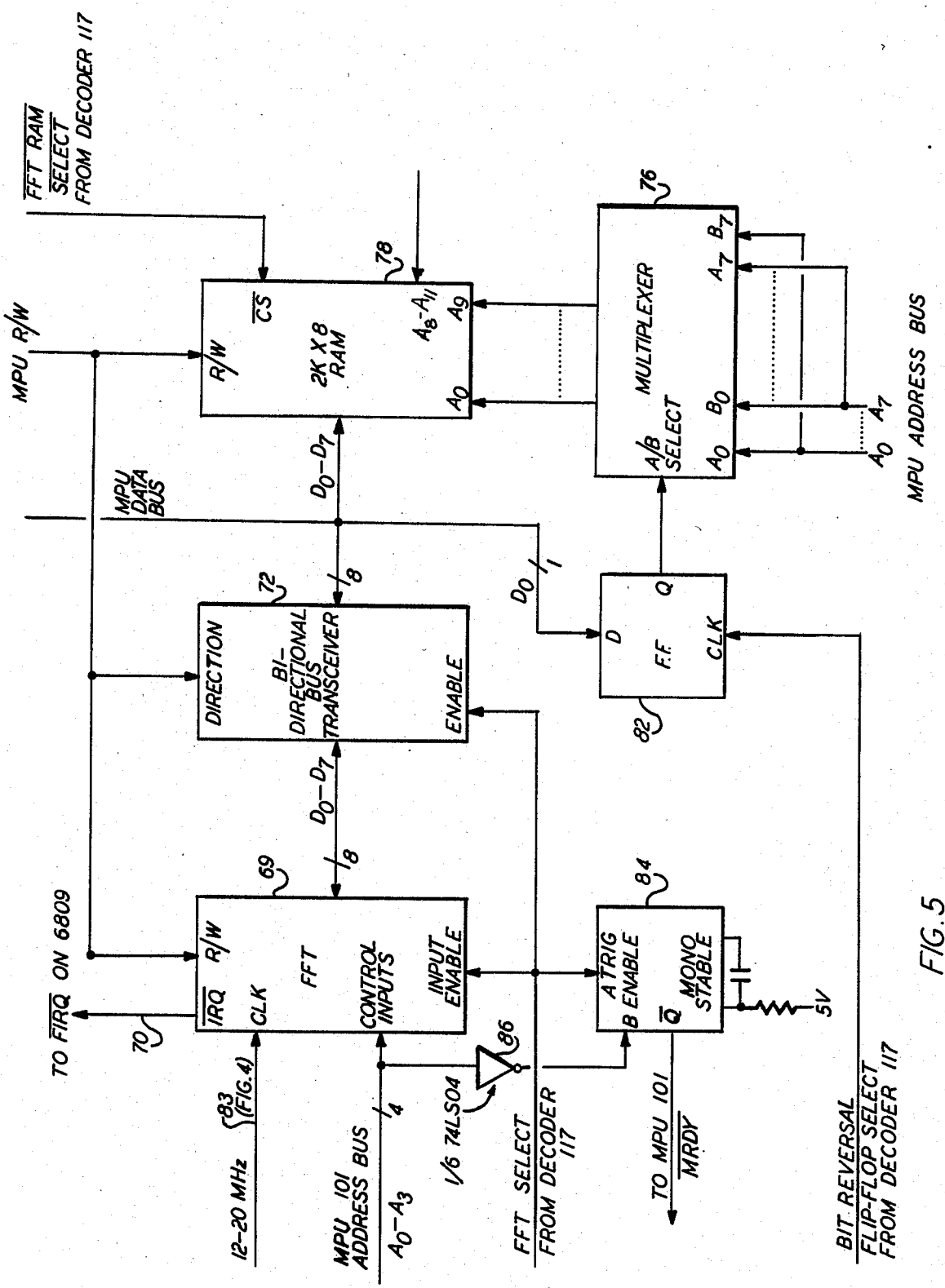
FIG. 5 is a block diagram of the FFT portion of FIG. 4 in more detail.

The actual process of FFT computation for a single channel is performed as follows with reference to FIG. 5. The higher order bytes of a segment of input data, 256 points (2.0 seconds) long, is first transferred to a FFT workspace located in random-access memory 78. The segment is subjected to a "windowing" algorithm, whose function is to minimize the effect on the final FFT results of potentially trunctated sine waves on either end of the data segment. To perform this algorithm, 5% of the data points on each end of the data segment are multiplied by a "cosine taper" function, effectively reducing their contribution to the resulting FFT. After windowing, the data segment is divided into blocks of 32 points using a procedure known as the decimation-in-frequency algorithm. This procedure is necessary because the FFT circuit 69 is designed to perform the FFT only on data blocks of 32 points per block. To perform the decomposition of the data segment, each sequential 32-point block of the segment is first loaded into the FFT circuit 69 through bidirectional bus transceiver 72 controlled from decoder 79 of FIG. 4. A command is then stored in circuit 69 to perform the decomposition routine. Circuit 69 notifies the microprocessor 67 via line 70 when it has finished the routine, and the microprocessor 67 then unloads the processed data. The procedure is then repeated for each of the remaining data blocks. After all blocks have been processed, the actual FFT algorithm is performed. Each block of data is loaded into circuit 69 and a command is then stored in circuit 69 to perform the FFT algorithm. When circuit 69 has completed processing, it notifies the microprocessor 67 that the data block may be unloaded. The data is stored in random-access memory 78 with its address bits reversed. This bit reversal algorithm is required to sort out the FFT data in the proper order. It is accomplished using three multiplexers, which may be 74LS157, indicated by block 76. Its A inputs have the address lines in proper order and its B inputs the address lines in reverse order. Selection of A or B inputs is on line 80 from D type flip flop 82 receiving an input of the RAM decoder 79 of FIG. 4. The output data from circuit 69 is the power spectrum of the input data. After the entire FFT algorithm has been performed, the output data is organized as N bins of 1/T Hz resolution, where N is the number of points in the input data segment, and T is the duration of the segment in seconds. The data in adjacent bins is summed to determine the total power in each of the four major EEG frequency bands plus any special frequency categories defined by the user. The square root of the total power in each frequency band is approximated to convert the power spectrum value into the magnitude spectrum value, a number which can be expressed directly in microvolts (a convenient unit of measurement for EEG analysis). The entire procedure just described is repeated for data segments for each of the 16 (28) input channels.

The nature of the FFT computation is such that the output data must be arranged in a different sequential fashion before being in proper order. The reordering can be performed in software or, for higher speed, in hardware. As described above in the disclosed system it is performed by hardware which reverses the address bits of dedicated RAM 78 set aside for the FFT output data. N bits are reversed for a 2 N point transform. For example, the 8 lowest bits are reversed for a 256 point transform. In practice, bit-reversal flip-flop 82 is set, selecting the "B" reversed multiplexer inputs, the FFT data is transferred into the RAM, and flip-flop 82 is then reset, applying the address bits to the RAM in their proper order.

For inputting certain types of command information on its control lines, the "Input Enable" line of circuit 69 requires a longer pulse from decoder 79 than would normally be produced were microprocessor 67 to be running at its 2 MHZ rate. Therefore, a monostable multivibrator 84 which may be a 74121, is used to stretch the microprocessor (MPU) internal clock when these certain commands are issued. This is detected through inverter 86 which is coupled to the address line A1 providing control inputs to circuit 69 which then enables monostable 84. The output of multivibrator 82 is connected to the "MRDY" line of the microprocessor 67. When this line is low, the MPU internal clock is stretched, effectively leaving the current address and data on their respective busses until the line returns high. The "Input Enable" line to circuit 69 is connected to the "A trigger" input of the monostable 84. Address line A1, inverted through inverter 86 as described above is connected to the "B enable" line of the monostable 84 so that a 1.5 microsecond negative pulse is generated only when "Input Enable" goes low and address A1 is also low. This condition is (fortuitously) present during the issuing of those commands which need longer "Input Enable" pulses. This feature is important because a great deal of the time spent doing the FFT is consumed in transferring the data in and out of the chip. If the MPU had to run at a uniformly slower speed to accomodate the longer "Input Enable" pulse requirement, throughput would seriously suffer.

MATCHED FILTER ANALYSIS

Another type of analysis performed by the EEG preprocessor is matched filter analysis. This type of analysis is based on the fact that if an inverse FFT is performed on the results of an FFT of digitized analog data, the output of the inverse FFT will be a perfect reconstruction of the original digitized data. Furthermore, if zeros are stored in bins of the initial FFT results containing undesired frequency components, the results of the subsequent inverse FFT will be the digitized analog input data with the undesired frequency components perfectly filtered out.

Thus, a pattern of interest in the EEG may be initially analyzed by means of the FFT and the resulting FFT pattern may be used as a template for detection of a similar signal in another sequence of EEG under investigation. For example, a spike-and-slow-wave event in the EEG of an epileptic may be visually identiied and analyzed by means of the FFT. The frequency bins containing low levels of activity in the results of this FFT are then determined. The template consists of a list of these bins, which are zeroed out in subsequent EEGs under investigation. The resuilt will be a reconstructed EEG containing values only in the frequency bins of interest.

Optionally, instead of zeroing out the bins with low values for the template, the template may be constructed by making the bin containing the highest value equal to 1.00, and all other bins as proportional fractions of 1.00. The subsequent EEGs under investigation will then be multiplied by this template.

In practice, an FFT is performed on a data segment of 256 points as described in the FFT analysis description. (As will be recalled, the result of the analysis will be contained in 256 bins, with each bin containing the power spectrum value for a 1/T Hz bandwidth, where T is the total duration of the data segment in seconds. In this case, at the 128 Hz sampling rate used, the data segment will be 2.0 seconds long and each of the 256 bins will have 0.5 Hz resolution. Thus, bin number 1 will have the magnitude spectrum of DC to 0.50 Hz, bin number 2 will have the value for 0.5–1.0 Hz, etc.) After the FFT is performed, the software places a value of zero or the template value of the preselected EEG event in each bin specified by the system user. Thus, if the user is interested in viewing the activity in the 12–16 Hz bandwidth, the program zeros the bins from DC to 11.5 Hz and from 16.5 Hz to 64 Hz (the upper limit of the FFT result).

The FFT module 69 performs the inverse FFT quite easily. Each block of input data is processed by the "CONJUGATE" routine, and then processed identically to digitized analog data as described in the FFT analysis section. The result of the entire procedure is a digitized signal which has been perfectly filtered (if the unwanted bins are zeroed), or which has been multiplied by the template. This procedure bypasses the disadvantages of high-order analog filters. The entire filtered waveform is transferred to the image processing and display unit and displayed as a continuous analog signal, similar to the manner in which evoked potentials are displayed. This allows an instant-by-instant localization of the frequency activity of interest on the topographical display.

The user may specify the template to be used through the terminal connected to the image generator and display unit. The template values are transferred to the EEG Preprocessor for use in the analysis of ongoing EEGs. Optionally, the user may specify that when a segment of EEG contains a segment of data highly matched to the template, the data segment should be retained in memory. This technique allows the automatic detection and retention of EEG events of neurological interest.

EVOKED POTENTIAL ANALYSIS

Finally, evoked potential analysis is possible. This is a signal averaging analysis of the EEG and has been an important investigative technique for neurologists for over 20 years. This technique involves the presentation of a stimulus, such as a light flash or tone burst to a subject and averaging the following 0.5 second to 1 second of EEG signal over many stimulus presentations. Since the major portion of the EEG occurs randomly with respect to the stimulus and may actually be considered noise, over a long period of time, it will average out to zero volts. On the other hand, the electrical activity specifically evoked by this stimulus is time locked to the sampling process and will be augmented by averaging over multiple trials. It is usually assumed that the portion of the signal that is augmented over many trials is directly related to and caused by the stimulus.

In order to perform an evoked response analysis on 16 channels of EEG, the signal processor of FIG. 4 first outputs a pulse suitable for triggering an external visual or auditory stimulus generator. This output on line 78 coupled through the decoder 79 is used to operate a stimulus generator. Each time a stimulus pulse is sent out, a set of 204 A to D conversions is performed on each EEG channel. This stimulus and acquisition sequence is repeated, typically every two seconds. The digital word from each conversion is simply added to the total of all previous values for that sample. The totals are stored as 3 bytes for each time point. The totals at the end of all trials are divided by the number of trials. In practice, the number of trials averaged for the computation is usually 256.

With whatever of the aforementioned types of preprocessing is carried out, one ends up with digital data for each of the 16 points. The results of this analysis are transferred to the image computation and display unit via the display microcomputer. In the image and computation display unit, actual generation of the topological map takes place. Transfer of data is over an 8 bit parallel interface through I/O buffers 73. A handshake protocol is used to facilitate data transfer. The preprocessor microcomputer notifies the display microcomputer that data is available and the display microcomputer responds when it is ready to accept data. A data header is first transferred, notifying the display microcomputer of the type of data processing which has been performed and the number of data bytes being transferred. The actual data is then transferred and consists of 16 bytes representing the levels of activity present at each of 16 electrode locations. The function of the image computation and display unit is to transform this array of points into a topographic map of the entire brain outline.

IMAGE COMPUTATION AND DISPLAY UNIT

Figure 6:
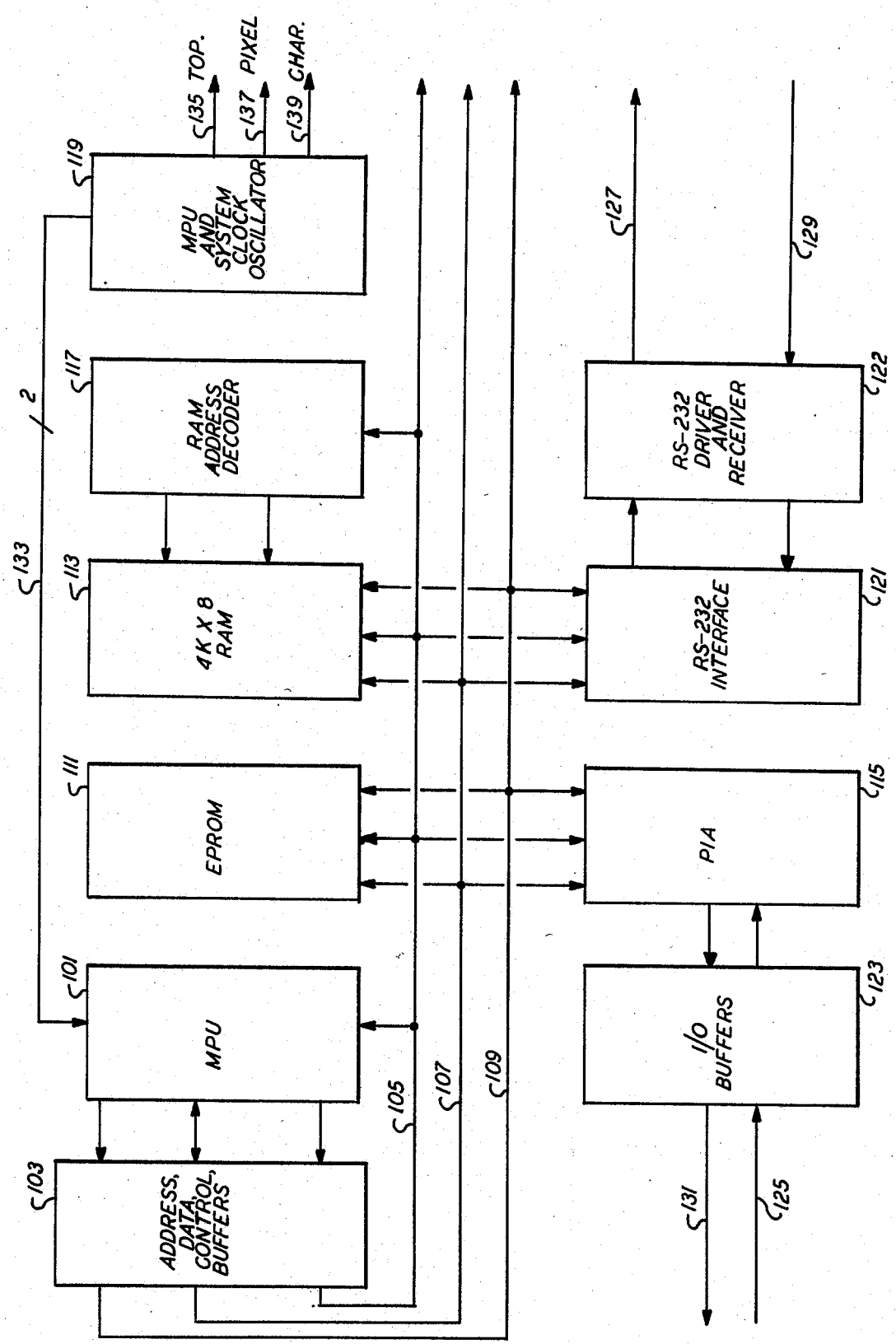
FIG. 6 is a block diagram of the image computation and display micro-computer.

The first portion of the image computation and display unit is illustrated in FIG. 6. A second microprocessor 101 is provided, which again can be a Motorola 68B09E Microprocessor. Associated with the microprocessor 101 through buffering unit 103 are the address bus 105, data bus 107 and control bus 109. Coupled to the buses is a 4 K byte EPROM 111 which contain the stored program. This may be an Intel 2732 EPROM. Also provided are $4K \times 8$ bytes of random access memory which can be made up of Motorola 2114 $1K \times 4$ byte RAMs. Also included is a peripheral interface adapter (PIA) 115 which can be made up of two Motorola 68B21 PIAs. The random access memory (RAM) 113 is addressed by a RAM address decoder which is made up of 74LS138 3–8 decoders and 74LS139 2–4 decoders. Also provided is a clock oscillator 119, which may be a quartz crystal and a 74LS04 inverter, an RS 232 interface 121, which may be a Motorola asynchronous communications interface adapter 68B50, and an RS 232 driver and receiver 122 coupled thereto to communicate with the terminal 20 of FIG. 1, and which can be made up of a 1488 RS232 driver and a 1489 RS232 receiver, and a Motorola K1135 baud rate generator. Buffering 103 is accomplished utilizing 74LS 244 Octal bus buffers for address and control lines and 74LS 245 Octal bus transceivers for data lines.

Information from the preprocessor is transferred in over line 125 and through the buffers 123 and peripheral interface adapter 113. The display microcomputer 101 accepts a set of 16 data points and formats them in 16 parallel data buffers in RAM 113. It passes appropriate sets of data points to the topographic map generator, to be described below, for updating of the brain image and initiates a topographic map computation cycle between 1 and 60 times per second.

As will be evident from the attached program, the software structure for the display microcomputer is interrupt driven. This means that the microcomputer performs tasks when notified through interrupts that the task is waiting. This arrangement facilitates efficient real time system operation. Interrupts are entered into the microprocess (MPU) 101 through the MPUS's IRQ (interrupt request), FIRQ (fast interrupt request), and NMI (non-maskable interrupt) pins. Typically, the FIRQ interrupt is generated by the RS-232 serial interface 121's IRQ output when a new character is ready to be read. The IRQ interrupt is generated by PIA 115 when data is ready to be received from the preprocessor of FIG. 4, and the NMI interrupt is generated by the "vert sync" output of the 6845 CRT controller (to be described below) at the start of each vertical blanking period. This facilitates having the MPU 101 operate in general synchrony with the display.

Furthermore, the display microcomputer drives the terminal 20 of FIG. 1. A typical terminal for user interaction may be a Hewlett-Packard 2621A CRT terminal with a standard RS-232 interface operating at 9600 baud. This is done through the RS-232 interface 121 and driver and receiver 122. Serial data is transmitted to the terminal over line 127 and received from the terminal over line 129. The attached program, resident in the PROM 111 allows the user to specify details of operation of the entire system. Two letter mnemonic commands followed by the appropriate number of numerical parameters control the EEG signal acquisition rate, artifact threshholds, the type of signal processing performed, signal characteristics of EEG events to be detected, the rate of topographic map updating, map colors, and all other important system parameters. The portions of this information necessary for use in the preprocessor are transferred over the line 131 to the preprocessor of FIG. 4.

The user is able to specify the details of data acquisition, processing, and display through a set of commands. The list of commands and their respective formats is known as a menu and can be displayed on the terminal screen at will. The commands are structured as two-letter mnemonic instructions followed, in most cases, by a parameter field containing one or more numerical parameters relating to the instruction. For example, to specify that the data to be displayed should be scanned through at a rate of 10 frames per second from data point 12 to data point 55, the user would type 'AS, 6, 12, 55' (Auto-Scan, interval in 1/60 sec. units, starting point, ending point). To display the color bar the user would type 'DB' (Display Bar, no parameters). A comprehensive list of commands and parameter formats is given at the beginning of the software listing.

Two data display modes are available, point mode and interpolation mode. In point mode, a map of a set of 16 (28) points is created as soon as the set is received, and that map is immediately displayed. For a more smoothly changing image, interpolation mode is used. In this mode, when a set of points is received from the preprocessor of FIG. 4, the difference between each of the 16 (28) points and the corresponding point in the last set is determined by subtraction. Next, the time between successive data transmissions times 30 is divided into this difference to determine the appropriate increment per frame. At each succeeding frame, this increment is added to the current point value, so that the data moves smoothly to its next value.

In addition to the display of the value of single frequency bands, other modes of display are possible. For example, it is possible to display the ratio of activity between two separate frequency bands as a color coded map. For example, since high alpha activity is characteristic of wakefulness and high delta activity is characterist of stages 3 and 4 (deep sleep) in the normal human sleep cycle, the ratio of alpha to delta amplitude might be displayed in an experiment tracing the progress of sleep stages over an entire night's sleep.

The difference between the activity at corresponding points on the two hemispheres may also be displayed on an image of a single hemisphere. This mode is extremely sensitive in displaying minute assymetries in hemisphere activity.

The system clock 119 shown in FIG. 6 includes a master oscillator operating at 14.318 MHz for use as the topographic generator master clock and as a character generator dot clock. The master oscillator frequency is divided down using a 74LS163 synchronous binary counter configured as a divide-by-9 counter to generate the 3.18 MHz video pixel clock and 1.59 MHz character clock. One of the outputs of the 74LS163 counter is also applied to a 74LS76 dual J-K flip-flop to generate the two 1.59 MHz clock signals required by the microprocessor 101, as indicated by the output on line 133. The outputs of the topographic map generator and for the video pixel clock and character clock are indicated as lines 135, 137 and 139, respectively.

The topographic map generator is illustrated in FIG. 7. Its purpose is to perform the high-speed numerical computations necessary to create and refresh the topographic map of EEG activity in real time. The computations are performed entirely by special purpose hardware. The generator accepts data for a set of points from the display microcomputer, which in turn has received these data points from the preprocessor. This data is loaded into a data buffer RAM 105 as described above. These points are measures of the activity of each of 16 positions over the scalp. Using these data points and a precomputed map file to be described in more detail below, the generator performs a linear interpolation to fill in all points on the brain image between the electrode positions.

In order to understand the operation of the topographic map generator, the basis of its creation must be understood. To create the map file, an anatomically accurate outline of a single hemisphere of the brain, [side view] or both brain hemispheres [top view] is drawn on an 80×100 unit rectilinear grid using a standard equal-area projection technique. FIG. 7A illustrates the side view and FIG. 7B the top view. This outline can be derived from any one of a number of anatomical atlas representatives of the brain. On this outline, the location of the internationally accepted "10-20" electrode positions 141 is precisely determined. The coordinates and outline of the electrode positions are then entered into a computer.

In order to create a standard map file which is to be stored on erasible programmable read-only memories, i.e., a 40K by 8 bit memory 143 such as shown in FIG. 7, an external micro or mini computer is connected to a EPROM programmer. To create a non-standard map file which is to reside in random access memory within the topographic map generator, the display microcomputer creates the file and stores it immediately in RAM. In such a case, the map file will generally be created when the entire system is first powered up or after entry from the CRT terminal by the user of non-standard data. In either case, all further computation necessary to create the map file is performed automatically by software. Thus, as indicated in FIG. 7, the map file 143 can be a preprogrammed EPROM or can be a random access memory (RAM) which is specially programmed in accordance with instructions from the user from the terminal under control of the microcomputer of FIG. 6.

In either case, as indicated by the attached software, for each grid element within the brain outline, the four nearest electrodes are located. It should be noted that each grid element will be represented by an individual pixel on the video display. In addition, the distance from the grid element to each of those electrode positions is determined. The contribution of the measured activity at each of those electrode positions to the total activity at the grid element under consideration is assumed to be in inverse linear proportion to the distance to the respective electrode divided by the four total electrode distances.

Using this procedure for each grid element a set of the four nearest electrode numbers and a corresponding set of four weight values, one for each of the electrodes, is generated. The set of four nearest electrode numbers for all the grid elements on the brain map is known as the electrode file. The set of weights for each of the electrodes for all the grid elements on the brain outline is known as the weight file. A third file known as the address file is established and is comprised of the frame buffer address of each of the corresponding grid elements on the brain outline. These three files together constitute the map file. Obviously, the electrode file and the weight file have four times as many data points as the number of grid elements in the brain outline. The address file has the same number of data points as the number of grid elements.

Preferably, standard map files are created for both single and dual hemisphere outlines of FIGS. 7 A & B and stored on Intel 2764 8K×8 bit erasable programmable read-only memories. These are the memories 143 shown in FIG. 6, with sufficient memories provided to obtain an 80K by 8 map file. When it is desired to use non-standard map files, e.g. using unusual electrode positions, the map files may be computed by the display microcomputer and stored on Hitachi 6116 2K×8 bit CMOS RAMS substituted for the EPROMS.

In either case, the organization of the map file is identical. Data for each element is organized as a 62 bit wide digital word. The configuration of each word is as follows: Weight 1 [7 bits]; electrode 1 [5 bits]; weight 2 [7 bits]; electrode 2 [5 bits]; weight 3 [7 bits]; electrode 3 [5 bits]; weight 4 [7 bits]; electrode 4 [5 bits]; frame buffer address [14 bits]. Since there are approximately 4,000 elements in the brain outline, 4,000×62 bits of memory is required. For the simultaneous storage of single and dual hemisphere maps on EPROM twice this amount of memory is required. The organization of the data for each grid element in the 62 bit wide parallel format facilitates the rapid sequence of computations required.

The process of filling in all 4,000 points on the brain outline is performed entirely by the elements illustrated in FIG. 7 permitting the brain image to be updated up to 60 times per second. This rapid updating allows the visualization of the travel of electrical activity patterns across the brain. To carry out the necessary linear interpolation to fill in all points, control counters and a programmable read only memory indicted as controller 145 are used. Controllor 145 is shown in more detail in FIG. 8. Preferably, the PROM 146 is a Harris HM7603 bipolar programmable read-only memory which operates at a very high speed. The outputs of the PROM are programmed to be the control signals for the circuits actually performing the computation. The PROM is addressed by a control counter made of two 74LS161 binary counters 148A and 148B receiving an input on line 135 from the clock at 14.315 HMHz. The outputs of the PROM are deglitched with a 74LS374 octal flip-flop unit 178 which is clocked after the address inputs of the PROM have settled so that the transitional addresses on the PROM inputs do not generate spurious outputs on the control lines.

The control PROM 146 circuit is responsible for outputting appropriate signals in the proper timing sequence to the computation and data circuitry in the topographic map generator. Control PROM 146 is a high-speed PROM specially programmed with a unique bit-pattern for this application. The outputs of the PROM place the appropriate data registers on the common busses at the right time, and also control the operation of the multiplier and the writing of the computation results into the frame buffer. As indicated above the PROM 146 address inputs are controlled by 5-bit synchronous counter made up of units 148A and 148B. The count of "17" is decoded by a section of a 74LS00 quad 2-input NAND gate 150, which decoded signal then resets the counters 148A and 148B to zero on the next clock pulse. Thus, there are 18 clock periods in the computation cycle for 1 pixel location.

Operation of the hardware of FIGS. 7 and 8 can best be understood through an example. Assume the beginning of a new image interpolation. Memory address counter 147 receiving an input from the controller 145 was reset between frame refreshes and thus is at 0. The outputs of address counter 147 provide the address inputs to the map file memory 143. With the memory counter address at 0, the first grid element is being computed. There are three groups of output lines from the map file memory 143. A group 149 of 20 lines couples outputs to electrode address flip-flops 151. A group 153 of 28 lines couples outputs to an electrode weight flip-flop 155 and a group 157 of 14 lines couples outputs to pixel address flip-flops 158. Each of blocks 151, 155 and 158 receive control inputs from controller 145 indicated by line 159. Electrode weight flip-flops in block 155 can be for example 74 LS374 octal flip-flops. These flip-flops each have 8 3-state outputs. Three-state outputs are of such a nature that they may assume either a logic 0 or a logic 1 and in addition, upon the application of an external control signal at an appropriate pin, the outputs are forced to a high impedance state, effectively isolating them from the output lines. Thus, many similar ICs may thus share the same physical lines with the appropriate ICs given control of those lines at the appropriate time. Such a scheme vastly simplifies the wiring and organization of large digital systems.

In block 155, the corresponding bit outputs of each of the four weight flip-flops is wired together on a common bus 161 known as the weight bus. The weight bus provides one input to a multiplier 163 which may be a TRW TDC 1008J 8×8 high-speed bipolar multiplier-accumulator. The second input to the multiplier is from a buffer random access memory 165 over line 167. This data buffer, which stores the data points from the preprocessor of FIG. 4 as transferred by microprocessor 101 of FIG. 6, receives its address input from a RAM address multiplexer 169 which in turn receives inputs from the electrode address flip-flops of block 151. Similarly, to the weight flip-flops, the electrode address flip-flops are wired together and provide inputs to the RAM address multiplexer which addresses the data buffer random access memory which has received from the microprocessor the value for each of 16 or 28 electrodes. Thus, the circuit 163 multiplies each electrode weight by the data value stored at the corresponding electrode RAM address.

Operation begins with a multiply enable command from decoder 117 into a flip-flop 158. This causes its Q output to go low to enable EPROM 143. Keeping the CE input high when EPROM 143 is not in use saves power. The Q output of flip-flop 158 is the J input to flip-flop 160. On the MPU 101 clock signal on line 133, this high at the Q output of flip-flop 158 is clocked into flip-flop 160. The output of flip-flop 160, thus synchronized with the MPU 101 clock, initiates the cycle by enabling counters 148A and 148B to start counting.

At the beginning of each cycle, "preload enable" goes high, gating a 74LS244 octal buffer 178, whose inputs are tied to ground, onto the output bus. The "preload enable" signal is also applied to the "PREL", "TSM", and "TSL" inputs of the multiplier, 103 of FIG. 7. These signals, in combination with "clock product" going high, force a zero into the output registers of the multiplier, initializing the result for this new computation. The rising edge of the "preload enable" signal also clocks the 62 bits from the map file EPROM 143 in parallel out into their respective flip-flop storage registers and also increments the map file EPROM address counters 147 to the next address.

The information is thus transferred into flip-flops 151, 155 and 158 under control of the controller 145. In other words, in accordance with the configuration given above, 7 bits times four are transferred to an octal flip-flop in block 155, the next 5 bits times four to a flip-flop in block 151, and the frame buffer address of 14 bits is transferred into the pixel address flip-flop block 158. Once the 62 bit parallel word has been clocked into the various flip-flops, the controller 145 increments the memory address counter so that the next parallel word starts to appear at the output of memory 143. At the same time, "Enable 1" goes low, gating the electrode weight #1 register 155 onto the multiplier X input bus 161, and gating the address of electrode #1 onto the data RAM 165 address input bus. (The value contained in that data RAM location is then gated onto the multiplier Y input bus 167). After a 1 clock delay for settling, the "clock X,Y" control line goes high, clocking the data at the X and Y inputs into the multiplier registers and performing the multiplication (X×Y). After a two clock delay for the multiplication result to become valid, the "clock product" line goes high, clocking the result into the output accumulator of the multipler 163. The PROM in the controller 145 then gives control of the weight bus to the flip-flop containing the second electrode weight and the control of the electrode bus to the flip-flop containing the address of the data from the second of the four nearest electrodes. This sequence is repeated for the remaining three electrodes weights and data values, with the result of each multiplication successively added to the value in the output accumulator. By the time the 4 multiplications have been completed, the "write enable" line has gone low, writing the 4 most significant bits of the result into the appropriate frame buffer location over line 177. At the end of 18 clock pulses, the PROM address counter is reset to zero, and the computation process repeated for the next pixel location. The final value stored in the accumulator represents the total value for the grid element under consideration. Since data scaling and rounding have already been performed, the top four bits in the accumulator can be stored directly in the frame buffer without further manipulation.

The frame buffer pixel address for the grid element whose value has just been computed is stored in the pixel address flip-flops 158. Referring to FIG. 9, the address can be applied over line 171 to the frame buffer address multiplexers 173, with the data applied to the frame buffer data buffers 175 over line 177. The computed value of the current grid element is thus applied to a frame buffer 179 through buffers 175 with the address supplied by the frame buffer address multiplexer 173 which includes an octal bus buffer. The control PROM in the controller 145 generates a "write enable" pulse thus writing the data just computed in the multiplier 163 into the memory location in the frame buffer 179 selected by the frame buffer 175 which in turn is addressed by the pixel address memory 158. This process is repeated for the other approximately 4,000 grid elements which make up the entire brain image. The multiplication accumulation-accumulation and memory storage for a single grid element requires 1.26 micro seconds to perform. An entire brain image of roughly 4,000 points may thus be computed in approximately 5.2 milliseconds.

VIDEO DISPLAY GENERATOR

Utilizing the computed information, the video display generator is now used to generate the appropriate signals for the high resolution video display. The elements of this portion of the system are illustrated in FIGS. 9, 10, and 11.

The video display generator is responsible for all functions relating to the actual display of the brain image and accompanying information on a color video display monitor. It operates under the control of the display microcomputer 101 of FIG. 6. The frame buffer 179 which is one of the main elements of the display generator is preferably made up of Motorola 2114 1K×4 bit random access memories. Also included are video display controller 181, for example, an Hitachi 68B45S video display controller which is used to control the frame buffer, the control output being indicated on line 183, through the frame buffer address multiplexers 173.

In addition, as illustrated in FIG. 10 there is provided a 2K×8 CMOS random-access memory 182 for storing alpha-numeric character information controlled by a second CRT controller 187. This controller also may be a 68B45S controller and the alpha-numeric memory can be made up of an Hitachi 6116 random-access memory. In addition, there is provided a character generator memory 189 which can be an INTEL 2716 EPROM.

The character generator circuit is thus controlled by its own video display controller 187. This allows text information to be formatted independantly of the main image contained in the frame buffer. The address outputs of controller 187 are applied to the A inputs of a character buffer address multiplexer 186 which may comprise 3 74LS157 quad 2-input multiplexers. The B inputs of multiplexer 186 are connected to lines A0–A10 of the MPU 101 address bus. The outputs of the multiplexers are connected to the address inputs of the 2K byte character buffer 182, which is a HM-6116, 2K×8 RAM. Both in the case of the main image frame buffer 179 of FIG. 9 and the present case, the address lines of the buffer RAM 182 are connected to the address lines of the video display controller on the first half of each clock cycle, and to the MPU 101 address lines on the second half of the cycle.

At the rising edge of the clock, the data being output by RAM 182 is clocked into a 74LS374 octal flip-flop 188. The outputs of this octal register are applied to the most significant address lines of the EPROM character generator 189. Character generator 189 has the dot matrix patterns of 128 alphanumeric and special characters stored on it. The 4 least significant address lines of the character generator 189 are connected to the row outputs R0–R3 of the video display controller 187. These row address lines are incremented at the end of each horizontal sweep, causing the pattern of the entire character to be shifted out row by row. The output of the character generator 189 is loaded into a 74LS165 shift register 190 through the shift register's parallel inputs. The dot clock on line 135 is applied to the shift register's clock input, clocking out the dot pattern for the particular character dot-by-dot on line 192. The Q output of the shift register on line 192 is applied through three 2K ohm resistors 194, 196, and 198 to the emitters of three 2N3640 PNP transistors 202, 204, and 206 operated in a common (grounded) base configuration. The collectors of the transistors are connected to the analog output of the red, green, and blue video D-A converters respectively. (See FIG. 11) The Q output of the shift register on line 192 is also connected to the "not force high" control input of all three D-A converters. Thus when a "1" is at the output of the shift register, the D-A converters work normally, and a fixed amount of current is injected through the transistors into the analog outputs. When a "0" is at the shift register output, the converters are all forced high, and the added current simultaneously removed through the 3 transistors. This action produces a white dot on the screen, with the amount of current removed regulating the brightness of the dot. The pattern of dots makes up the perceived character.

The final video output to the display is from these video D to A converters 191, 193 and 195 (shown in FIG. 11). These in turn each receive their digital data from random access memories 197, 199 and 201, respectively. The outputs of the memories 197, 199 and 201 are applied respectively to the digital-to-analog converters 191, 193 and 195. The resulting voltages are applied to the video monitors color guns. The voltages are directly proportional to the components of red, green and blue in the color specified by the color transformation data. The output of the alphanumeric character generator is mixed directly with the D to A converter outputs as an analog voltage using the transistors described above. The added voltage creates the white dots which make up the dot matrix of each display character on the video screen. The ouputs of the D to A converter are connected to the monitor inputs through standard 75 ohm video coaxial cable.

The D to A converters can be TRW TDC1016 video speed digital to analog converters. The memories supplying data to the converters may be made up of 74LS189 16×4 bit random access memories. The random access memories 197, 199 and 201 are addressed by RAM address multiplexers 203 and 207. Inputs into the RAM address multiplexer 203 are obtained through the frame data buffer set of flip-flops indicated by block 209 of FIG. 9. In addition, both address multiplexer 203 and address multiplexer 207 may be addressed from the microprocessor 101 of FIG. 6. The address multiplexers may be 74 LS157 units and the frame buffer flip-flops 74LS173.

The frame buffer concept utilized in the present system is based on a large random access memory in which a separate memory location is dedicated to each graphic element [pixel] displayed on the screen. The digital bits stored in each memory location specify the color of the pixel at a corresponding location on the screen. By displaying the contents of each memory location sequentially in synchronization with the sweep of the video raster over the screen, a video image is created. Frame buffer 179 in the present system is made up of 16 1K×4 bit random access memories. It is organized as 132 horizontal elements by 100 vertical elements. The extra elements in the frame buffer may be used for upward and downward scrolling of the image. Each element is 4 bits wide allowing the simultaneous display of 16 distinct colors on the screen. The CRT controller 181 carries out the task of sequential frame buffer memory addressing and video raster synchronization in conventional fashion. This controller 181 receives an input on line 137 from the system clock 119 of FIG. 5. On each successive clock pulse, it addresses the next sequential memory location in the frame buffer. The video display generator formats the frame buffer addresses so that the entire frame buffer is addressed exactly once every video frame. To facilitate the process, the video generator also generates horizontal and vertical sync pulses on lines 211 and 213 which tell the monitor when to begin each new horizontal scan line and when to begin each new frame. In practice, the vertical and horizontal sync signals are combined into a single signal by means of a 74LS02 NOR gate. The monitor internally separates the two sync signals.

The system provides an interleaved frame buffer access which permits the frame buffer memory 179 to be addressed at appropriate times by the video display controller 181 which is responsible for the sequential display of frame buffer memory locations in sync with the video raster scan, the display microprocessor 101 which is responsible for the creation of all graphics information except the brain image, and the topographic map generator on line 171 which deposits in the appropriate frame buffer locations the actual image of the brain with the appropriate color information in each location. The need to allow these multiple address sources access to the frame buffers is simplified by the fact that the microprocessor 101 is able to access memory only on the second half of each clock cycle. Therefore, the first half of each clock cycle can always be used by the video display controller 181 to access sequential memory locations, insuring a continuous "snow-free" display on the video screen. During the period that the topographic map generator is actively computing brain image values, it is granted access to the frame buffer during the second half of each clock cycle. At all other times, the display microcomputer is granted acccess during the second half of each clock cycle. The interleaved access may be accomplished by using an array of 74LS153 dual 4-input digital multiplexers as a frame buffer address multiplexer 173.

Again, operation of this portion of the system can be better understood by means of an example. To do this, the events occurring during a typical clock cycle will be examined. Assume that the topographic map generator of FIG. 7 is in the midst of a computation cycle. Access to the frame buffer 179 will therefore be shared by the video display controller 181 during the first half of each cycle and the topographic map generator during the second half of each cycle. When the clock goes from a digital 1 to a digital 0 a new clock cycle is initiated. The falling clock edge increments the address outputs of the video display controller 181 which the address multiplexer 173 has now connected to the frame buffer memory 179 inputs. After the access time of the frame buffer memories has elapsed, the data corresponding to the address locations appears at the data outputs of the frame buffer 179. This data is latched by the frame buffer latch 209 which comprise 74LS173 quad flip-flops. At the end of the first half of the clock cycle, the clock level goes from 0 to 1 and the multiplexer connects the frame buffer address inputs to the address of the current frame buffer location whose color has just been computed by the topographic map generator. After a short delay, the topographic map generator generates a short write-enable pulse storing the color value data it has just computed into the frame buffer location being addressed. During the times that the topographic map generator is inactive, the display microcomputer is given access to the frame buffer in similiar fashion during the second half of each clock cycle. The great advantage of this interleaved system of memory access is that even though access to the frame buffer is relinquished by the video display generator on each clock cycle, no evidence of this fact is visible on the screen. The video display remains free of noise or any visual abnormalities.

The memories 197, 199, and 219 comprise color transformation memories. As indicated previously, the data for each pixel is contained in the four bit wide frame buffer memory location 179. Instead of directly converting this value to analog voltages for driving the monitors color guns, the four bit value is used to address a 16×12 bit color transformation memory made up as indicated in FIG. 9 of 3 16×4 bit memories 197, 199 and 201, each representing one of the three colors—red, green and blue. In each of the 16 locations in this memory, is a 12 bit word specifying a single color, 4 bits specifying a red, blue and green components of the color. It is the output of the color transformation memory which is applied to the three video digital to analog converters 191, 193 and 195. The advantage of this arrangement is that while the number of colors that may be displayed on the screen at one time is still 16, the 16 colors may be selected from a range of 4096 colors (i.e. $2^{12}$). Selection is accomplished under microprocess control through terminal 20 of FIG. 1 utilizing data lines 196 with the memory locations addressed over line 105. For a given set of processing color assignments are fitted. This change which is made in memories 197, 199 and 201 is done when setting up the system.

FIG. 12 shows a typical display generated by the system of the present invention. Adjacent the display of the brain image 301 is a color scale 303 comprising small rectangular swatches of each of the 16 possible display colors. Alongside each swatch is a number representing the value that that color represents on the topographic map. Color values are computed and displayed automatically under control of the display microcomputer of FIG. 5. The character display seen in FIG. 12 is generated utilizing the controller 187, memory 182 and alpha-numeric generator 189 of FIG. 10.

A status line is continuously displayed at the bottom of the video screen notifying the user of various aspects of system operation such as display scan rate, frame number, and total elapsed data time. A time bar may be displayed at the user option, which consists of a displayed arrow moving across a horizontally displayed bar. This informs the user which points in the captured sample sequence is being displayed at that instant.

A typical video monitor may be a Mitsubishi C-3910 19" RGB delta-gun high resolution color video monitor. In any case, the monitor used must be capable of 19 KHz horizontal sweep frequency.

What is claimed is:

1. A fast Fourier transform (FFT) circuit comprising:
   (a) a microprocessor;
   (b) a program memory for said microprocessor;
   (c) a first random access memory for said microprocessor;
   (d) an address decoder for said first random access memory;
   (e) clock means for providing clock inputs to said microprocessor;
   (f) input/output ports, said units coupled together by means of address, data and control busses;
   (g) a plurality of signals in digital form to be transformed being an input to one of said input/output ports;
   (h) an FFT module receiving a digital word and performing a fast Fourier transform on said word;
   (i) a bidirectional buss transceiver for providing data to and receiving data from said FFT module having one of its data inputs coupled thereto;
   (j) an FFT random access memory coupled to said data and control busses, said data busses also coupled to the other data input of said bidirectional bus transceiver;
   (k) an FFT multiplexer coupling the address lines from said address bus for said random access memory into said FFT random access memory permitting inputting the addresses in normal order, and, upon selection, reverse order; and
   (l) means receiving an output from said address decoder and providing an input to said FFT multiplexer for said selecting between a normal order and a reverse order one for use during input of data to said FFT module and the other for use after data has been converted by said FFT module.

2. Apparatus according to claim 1 and further including means to convert the clock signal from said clock means into a signal of sufficient length to carry out the FFT in said module to thereby avoid slowing down processing by said first microprocessor.

3. Apparatus according to claim 2 wherein said means to convert comprise a monostable multivibrator receiving an enable input from one address line and a trigger input from a FFT select output of said first address decoder, said monostable multivibrator set to have a time out period equal to the period required to meet the input data hold requirements of the FFT module.

4. A method of performing an Fast Fourier Transform (FFT) on an M point data segment comprising:
   (a) storing digital signals corresponding to the M points to be transformed in a random access memory;
   (b) transferring an N point data block from said first random access memory to an FFT module for performing a transform on N points, using a microprocessor and through a bidirection bus transceiver controlled by said microprocessor, where M is equal to N times P where P is an integer equal to or greater than 2;
   (c) performing an FFT in said FFT module on said N points under command of said microprocessor;
   (d) transferring the transformed N point data block from said FFT to an FFT random access memory through said bus transceiver using said microprocessor;
   (e) carrying out steps (b) to (d) P times so as to completely transform said M points of data;
   (f) unloading the transformed data from said FFT random access memory to said first random access memory using said microprocessor; and
   (g) multiplexing address lines into said FFT random access memory between a normal order and a reverse order, one of said orders being used during input of data to said FFT random access memory and the other during unloading of data from said FFT random access memory to said first random access memory.

5. The method of claim 4 wherein said microprocessor has an internal clock signal, during one state of which data and addresses at the output of said microprocessor remain valid, and further including stretching said clock signal whom transferring signals to and from said FFT module to a signal of sufficient length to carry out data transfer with said FFT module to thereby avoid slowing down processing by said microprocessor at other times.

6. The method of claim 4, wherein said FFT module is capable of performing different sequences of sub-routines on the data supplied to it and further including selecting a sequence of sub-routines to be performed on said data by said FFT module through writing of an address to said FFT module with the microprocessor.

7. The method of claim 4 wherein N is equal to 32.

8. The method according to claim 4, wherein said FFT module transforms data using a decimation-in-frequency algorithm.

* * * * *